United States Patent
Morton

(10) Patent No.: US 9,642,800 B2
(45) Date of Patent: May 9, 2017

(54) DRY POWDER INHALER FORMULATIONS COMPRISING SURFACE-MODIFIED PARTICLES WITH ANTI-ADHERENT ADDITIVES

(71) Applicant: VECTURA LIMITED, Chippenham (GB)

(72) Inventor: David Morton, Chippenham (GB)

(73) Assignee: VECTURA LIMITED, Chippenham, Wiltshire (GB)

( * ) Notice: Subject to any disclaimer, the term of this patent is extended or adjusted under 35 U.S.C. 154(b) by 0 days.

(21) Appl. No.: 14/823,484

(22) Filed: Aug. 11, 2015

(65) Prior Publication Data
US 2016/0000709 A1 Jan. 7, 2016

Related U.S. Application Data

(63) Continuation of application No. 13/085,200, filed on Apr. 12, 2011, which is a continuation of application No. 11/791,385, filed as application No. PCT/GB2005/050211 on Nov. 23, 2005, now abandoned.

(30) Foreign Application Priority Data

Nov. 23, 2004 (GB) .................................. 0425758.0

(51) Int. Cl.
| | | |
|---|---|---|
| A61K 31/55 | (2006.01) | |
| A61M 15/00 | (2006.01) | |
| A61K 31/473 | (2006.01) | |
| A61K 31/135 | (2006.01) | |
| A61K 47/26 | (2006.01) | |
| A61K 47/12 | (2006.01) | |
| A61K 9/14 | (2006.01) | |
| A61K 31/522 | (2006.01) | |
| A61K 9/00 | (2006.01) | |
| A61K 31/58 | (2006.01) | |

(52) U.S. Cl.
CPC ............ *A61K 9/0075* (2013.01); *A61K 9/145* (2013.01); *A61K 31/135* (2013.01); *A61K 31/473* (2013.01); *A61K 31/522* (2013.01); *A61K 31/55* (2013.01); *A61K 31/58* (2013.01); *A61K 47/12* (2013.01); *A61K 47/26* (2013.01); *A61M 15/0028* (2013.01); *A61M 2202/064* (2013.01)

(58) Field of Classification Search
CPC ...... A61K 9/0075; A61K 9/145; A61K 31/58; A61K 31/55; A61K 31/522; A61K 31/473; A61K 31/135; A61K 47/26; A61K 47/12; A61M 15/0028
See application file for complete search history.

(56) References Cited

U.S. PATENT DOCUMENTS

| | | |
|---|---|---|
| 4,687,773 A | 8/1987 | Neumeyer |
| 5,292,520 A | 3/1994 | De Haan et al. |
| 5,441,747 A | 8/1995 | De Haan et al. |
| 5,655,523 A | 8/1997 | Hodson et al. |
| 6,029,662 A | 2/2000 | Marcon |
| 6,045,828 A | 4/2000 | Bystrom et al. |
| 6,051,257 A | 4/2000 | Kodas et al. |
| 6,475,523 B1 | 11/2002 | Staniforth |
| 6,528,096 B1 | 3/2003 | Musa et al. |
| 6,528,521 B2 | 3/2003 | Ruff et al. |
| 6,989,155 B1 | 1/2006 | Ganderton et al. |
| 2002/0002176 A1 | 1/2002 | Gupta et al. |
| 2002/0035993 A1 | 3/2002 | Edwards et al. |
| 2002/0071871 A1 | 6/2002 | Snyder et al. |
| 2002/0086876 A1 | 7/2002 | Ruff et al. |
| 2002/0127188 A1 | 9/2002 | Platz et al. |
| 2003/0017115 A1 | 1/2003 | Rabinowitz et al. |
| 2003/0055034 A1 | 3/2003 | Mongomery |
| 2003/0113272 A1 | 6/2003 | Staniforth |
| 2003/0157182 A1 | 8/2003 | Staniforth et al. |
| 2003/0162835 A1 | 8/2003 | Staniforth et al. |
| 2003/0165436 A1 | 9/2003 | Staniforth et al. |
| 2003/0175214 A1 | 9/2003 | Staniforth et al. |
| 2003/0175355 A1 | 9/2003 | Tobyn et al. |
| 2003/0185764 A1 | 10/2003 | Staniforth et al. |
| 2003/0186843 A1 | 10/2003 | Staniforth et al. |

(Continued)

FOREIGN PATENT DOCUMENTS

| | | |
|---|---|---|
| AU | 2001291122 | 4/2002 |
| CN | 1179097 | 4/1998 |
| CN | 1326341 | 12/2001 |
| CN | 1972730 | 5/2007 |
| EP | 0931595 | 7/1999 |
| EP | 0954282 | 11/1999 |
| EP | 1159955 | 12/2001 |
| EP | 1213012 | 6/2002 |
| GB | 2353222 | 2/2001 |
| JP | 2001072586 | 3/2001 |

(Continued)

OTHER PUBLICATIONS

Peart J. et al. "Multicomponent Particle Interactions in Dry Powder Aerosols." Pharmaceutical Research, Spring New York LLC, US, vol. 14, No. 11-S, Jan. 1, 1997, pp. S142-S143, XP001030455.

(Continued)

*Primary Examiner* — Suzanne Ziska
*Assistant Examiner* — Thurman Wheeler
(74) *Attorney, Agent, or Firm* — Matthew S. Gibson; Reed Smith LLP

(57) ABSTRACT

The present invention is concerned with a refinement of the processing of particles that are to form a dry powder formulation which is to be administered to the lung using a dry powder inhaler (DPI) device. In particular, the present invention provides the processing of particles of active material and particles of carrier material in the presence of additive material to provide a powder composition which exhibits excellent powder properties and which is economical to produce.

16 Claims, 7 Drawing Sheets

(56) References Cited

U.S. PATENT DOCUMENTS

| | | |
|---|---|---|
| 2004/0028613 A1 | 2/2004 | Quay |
| 2004/0037785 A1 | 2/2004 | Staniforth et al. |
| 2004/0047810 A1 | 3/2004 | Staniforth et al. |
| 2004/0052733 A1 | 3/2004 | Staniforth et al. |
| 2004/0071635 A1 | 4/2004 | Staniforth et al. |
| 2004/0204439 A1 | 10/2004 | Staniforth |
| 2004/0204440 A1 | 10/2004 | Staniforth |
| 2005/0013862 A1 | 1/2005 | Tobyn et al. |
| 2005/0152849 A1 | 7/2005 | Staniforth |
| 2005/0261163 A1 | 11/2005 | Tobyn et al. |
| 2006/0127480 A1 | 6/2006 | Tobyn et al. |
| 2006/0147389 A1 | 7/2006 | Staniforth et al. |
| 2006/0257491 A1 | 11/2006 | Morton et al. |
| 2006/0292081 A1 | 12/2006 | Morton et al. |
| 2007/0065373 A1 | 3/2007 | Morton et al. |
| 2007/0081948 A1 | 4/2007 | Morton et al. |
| 2010/0209358 A1 | 8/2010 | Staniforth |

FOREIGN PATENT DOCUMENTS

| | | | |
|---|---|---|---|
| JP | 2001151673 | 6/2001 | |
| JP | 2003530344 | 10/2003 | |
| JP | 2003530425 | 10/2003 | |
| JP | 2004509141 | 3/2004 | |
| JP | 2004514504 | 5/2004 | |
| WO | 9116038 | 10/1991 | |
| WO | 9500127 | 1/1995 | |
| WO | 9623485 | 8/1996 | |
| WO | WO9623485 | * 8/1996 | ............. A61K 9/00 |
| WO | 9632149 | 10/1996 | |
| WO | 9703649 | 2/1997 | |
| WO | 9831346 | 7/1998 | |
| WO | 0027363 | 5/2000 | |
| WO | 0033811 | 6/2000 | |
| WO | 0072827 | 12/2000 | |
| WO | 0100262 | 1/2001 | |
| WO | 0113893 | 3/2001 | |
| WO | 0149263 | 7/2001 | |
| WO | 0176575 | 10/2001 | |
| WO | 0178693 | 10/2001 | |
| WO | 0178694 | 10/2001 | |
| WO | 0178695 | 10/2001 | |
| WO | 0178696 | 10/2001 | |
| WO | 0182906 | 11/2001 | |
| WO | 0195874 | 12/2001 | |
| WO | 0200197 | 1/2002 | |
| WO | 0207805 | 1/2002 | |
| WO | 0243693 | 6/2002 | |
| WO | 0243701 | 6/2002 | |
| WO | 02067902 | 9/2002 | |
| WO | 02089880 | 11/2002 | |
| WO | 02089881 | 11/2002 | |
| WO | 2004089374 | 10/2004 | |
| WO | 2004093848 | 11/2004 | |
| WO | 2005025541 | 3/2005 | |
| WO | 2005063203 | 7/2005 | |
| WO | 2005099674 | 10/2005 | |
| WO | 2005105043 | 11/2005 | |
| WO | 2006059152 | 6/2006 | |

OTHER PUBLICATIONS

Kawaskima et al. "Design of inhalation dry powder of pranlukast hydrate to improve dispersibility by the surface modification with light anhydrous silicic acid (Aerosil 200)." International Journal of Pharmaceutics, vol. 173, No. 1-2, Oct. 1, 1998, pp. 243-251, XP0551909780.

Amendment and Response to Office Action filed in U.S. Appl. No. 13/464,445 on Nov. 10, 2014.

Final Rejection issued in U.S. Appl. No. 13/464,445 on Jul. 8, 2014.

Wennerstrum, et al. "Size Reduction Solutions for Hard-to-Reduce Materials." Powder and Bulk Engineering. Jan. 2002.

Kodas et al., "Aerosol Processing of Materials." Chapter 13, pp. 436-491 (1999).

Amann et al., "Comprehensive Pharmacy Review." Pharmaceutical Sciences, Part 1, Chapter I, Drug Product Development in the Pharmaceutical Industry. pp. 1-6, 3rd Edition, (1997).

Lucas et al., "Enhancement of Small Particle Size Dry Powder Aerosol Formulations Using an Ultra-Low Density Additive." Pharmaceutical Research, vol. 16, No. 10, pp. 1643-1647 (1999).

"Ensuring Patient Care, The Role of the HFC MDI." International Pharmaceutical Aerosol Consortium, 2nd Edition, pp. 1-56 (Jun. 1999).

Ashurst et al., "Latest Advances in the Development of Dry Powder Inhalers." Pharm. Science Technology Today, vol. 3, No. 7, pp. 246-256 (2000).

R. Pfeffer et al. "Synthesis of engineered particulates with tailed properties using dry particle coating." Powder Technology 117 (2001) 40-67.

Translation of Chinese Office Action dated Feb. 1, 2016 for Chinese Patent Application No. 201410314552.X.

Translation of Chinese Search Report dated Feb. 1, 2016 for Chinese Patent Application No. 201410314552.X.

Zhenwang, "Analysis of the Research Progress of Dry Powder Inhalant from List Product." Herald of Medicine, vol. 26, No. 3, Mar. 31, 2007.

Zeng et al., "Particulate interactions in dry powder formulations for inhalation" Taylor & Francis, 2001, London, p. 240-244.

Zhenwang, "Analysis of the Study Progress of Dry Powder Inhalations from Commercial Available Products." Herald of Medicine, vol. 26. No. 3, Mar. 31, 2007.

* cited by examiner

Table 1 - Hosokawa Powder Tester Results - Sorbolac 400 (Mechanofused)

| Parameter | Sorbolac | Mechano-Fused Sorbolac | Mechano-Fused Sorbolac + MgSt (98:2) | Mechano-Fused Sorbolac + MgSt (98:2) | Mechano-Fused Sorbolac + MgSt (98:2) | Mechano-Fused Sorbolac + MgSt (95:5) | Low Shear Mixed Sorbolac + MgSt (98:2) |
|---|---|---|---|---|---|---|---|
| Time | N/A | 60 mins | 5 mins | 10 mins | 60 mins | 60 mins | 15 mins |
| Angle of Repose (°) | 55.7 | 52.9 | 45.8 | 46.6 | 42.0 | 40.9 | 60.3 |
| Angle of Fall (°) | 46.8 | 40.2 | - | - | 24.3 | 27.1 | 45.1 |
| Angle of Difference (°) | 8.9 | 12.7 | - | - | 17.7 | 13.8 | 15.2 |
| Aerated Bulk Density (g/ml) | 0.248 | 0.294 | - | 0.629 | 0.654 | 0.639 | 0.261 |
| Packed Bulk Density (g/ml) | 0.612 | 0.641 | - | 0.938 | 0.974 | 0.962 | - |
| Compressibility (%) | 59.5 | 54.1 | - | 32.9 | 32.9 | 33.6 | - |
| Dispersibility (%) | 8.5 | 12.7 | 60.3 | 58.0 | 61.4 | 66.8 | 59.3 |

Fig. 2

Table 2 - Hosokawa Powder Tester Results - Extra Fine Lactose

| Parameter | Extra Fine Lactose | Extra Fine Lactose + MgSt (98:2) |
|---|---|---|
| Time | N/A | 60 mins |
| Angle of Repose (°) | 53.6 | 40.1 |
| Angle of Fall (°) | 42.5 | 22.3 |
| Angle of Difference (°) | 11.1 | 17.8 |
| Aerated Bulk Density (g/ml) | 0.324 | 0.719 |
| Packed Bulk Density (g/ml) | 0.745 | 1.035 |
| Compressibility (%) | 56.5 | 30.5 |
| Dispersibility (%) | 16.1 | 69.6 |

Fig. 3

Table 3 - Hosokawa Powder Tester Results - Sorbolac 400 (Cyclomixed)

| Parameter | Sorbolac | Cyclomixed Sorbolac + MgSt (98:2) | Cyclomixed Sorbolac + MgSt (98:2) | Cyclomixed Sorbolac + MgSt (98:2) | Cyclomixed Sorbolac + MgSt (99:1) | Cyclomixed Sorbolac + MgSt (95:5) | Mechno-Fused Sorbolac + MgSt (98:2) | Mechno-Fused Sorbolac + MgSt (95:5) |
|---|---|---|---|---|---|---|---|---|
| Time | N/A | 0 mins | 10 mins | 60 mins | 60 mins | 60 mins | 60 mins | 60 mins |
| Angle of Repose (°) | 55.7 | 49.0 | 50.0 | 46.1 | 52.7 | 51.9 | 42.0 | 40.9 |
| Angle of Fall (°) | 46.8 | 36.5 | 40.4 | 31.0 | 35.3 | 33.3 | 24.3 | 27.1 |
| Angle of Difference (°) | 8.9 | 12.5 | 9.6 | 15.1 | 17.4 | 18.6 | 17.7 | 13.8 |
| Aerated Bulk Density (g/ml) | 0.248 | 0.328 | 0.562 | 0.557 | - | - | 0.654 | 0.639 |
| Packed Bulk Density (g/ml) | 0.612 | - | - | - | - | - | 0.974 | 0.962 |
| Compressibility (%) | 59.5 | - | - | - | - | - | 32.9 | 33.6 |
| Dispersibility (%) | 8.5 | 58.9, 68.1 | 43.7 | 56.6, 73.1 | 51.4 | 34.3 | 61.4 | 66.8 |

Fig. 4

Table 4 - Hosokawa Powder Tester Results - Micronised Lactose (Model Drug)

| Parameter | Micronised Lactose | Mechanofused Micronised Lactose + Mg St (95:5) (blend) | Mechanofused Micronised Lactose + Mg St (90:10) (blend) | Mechanofused Micronised Lactose + Mg St (80:20) | Mechanofused Micronised Lactose + Mg St (80:20) 2mm gap |
|---|---|---|---|---|---|
| Time | N/A | 30 mins | 30 mins | 30 mins | 30 mins |
| Angle of Repose (°) | 23.5 | 51.0 | 53.6 | 47.5 | 55.8 |
| Angle of Fall (°) | 33.0 | 45.3 | 42.6 | 28.1 | 42.0 |
| Angle of Difference (°) | -9.5 | 5.7 | 11.0 | 19.4 | 13.8 |
| Aerated Bulk Density (g/ml) | 0.172 | 0.361 | 0.346 | 0.275 | 0.267 |
| Packed Bulk Density (g/ml) | 0.396 | - | - | 0.551 | 0.540 |
| Compressibility (%) | 56.6 | - | - | 50.1 | 50.6 |
| Dispersibility (%) | 6.0 | 28.4 | 25.5 | 37.6 | 46.5 |

Fig. 5

Table 5 - Hosokawa Powder Tester Results - SV003 (Conventional "Large" Carrier)

| Parameter | SV003 | Mechano-Fused SV003 + MgSt (99:1) | Mechano-Fused SV003 + MgSt (99:1) | Mechano-Fused SV003 + MgSt (99:1) | Mechano-Fused SV003 + MgSt (98:2) | Mechano-Fused SV003 + MgSt (98:2) |
|---|---|---|---|---|---|---|
| Time | N/A | 60 mins | 60 mins | 60 mins | 60 mins | 60 mins |
| Angle of Repose (°) | 44.0 | 36.3 | 38.1 | 35.9 | 43.1 | 42.2 |
| Angle of Fall (°) | 29.0 | 30.9 | 33.9 | 30.8 | 33.3 | 35.3 |
| Angle of Difference (°) | 15.0 | 5.4 | 4.2 | 5.1 | 9.8 | 6.9 |
| Aerated Bulk Density (g/ml) | 0.637 | 0.730 | 0.738 | 0.740 | 0.748 | 0.747 |
| Packed Bulk Density (g/ml) | 0.769 | 0.874 | 0.878 | 0.877 | 0.905 | 0.907 |
| Compressibility (%) | 17.2 | 16.5 | 15.9 | 15.6 | 17.3 | 17.6 |
| Dispersibility (%) | 7.7 | 14.2 | 12.6 | 11.9 | 22.1 | 7.3 |

Fig. 6

DRY POWDER INHALER FORMULATIONS COMPRISING SURFACE-MODIFIED PARTICLES WITH ANTI-ADHERENT ADDITIVES

RELATED APPLICATIONS

This application is a continuation of U.S. application Ser. No. 13/085,200 filed Apr. 12, 2011, which is a continuation of U.S. application Ser. No. 11/791,385 filed Jul. 5, 2007, now abandoned which is a United States national stage of International Application No. PCT/GB2005/050211, filed Nov. 23, 2005, which was published as International Publication No. WO 2006/056812, and which claims benefit of United Kingdom Application No. 0425758.0 filed, Nov. 23, 2004, the entire contents of which are hereby expressly incorporated herein by reference thereto.

FIELD OF THE INVENTION

The present invention is concerned with a refinement of the processing of particles that are to form a dry powder formulation which is to be administered to the lung, for example using a dry powder inhaler (DPI) device. In particular, the present invention provides the processing of particles of active material and particles of carrier material in the presence of additive material to provide a powder composition which exhibits excellent powder properties and which is economical to produce.

BACKGROUND OF THE INVENTION

Inhalation represents a very attractive, rapid and patient-friendly route for the delivery of systemically acting drugs, as well as for drugs that are designed to act locally on the lungs themselves. It is particularly desirable and advantageous to develop technologies for delivering drugs to the lungs in a predictable and reproducible manner.

The key features which make inhalation an exciting drug delivery route are: rapid speed of onset; improved patient acceptance and compliance for a non-invasive systemic route; reduction of side effects; product life cycle extension; improved consistency of delivery; access to new forms of therapy, including higher doses, greater efficiency and accuracy of targeting; and direct targeting of the site of action for locally administered drugs, such as those used to treat lung diseases such as asthma, COPD, CF or lung infections.

However, the powder technology behind successful dry powders and DPI products remains a significant technical hurdle to those wishing to succeed with this route of administration and to exploit the significant product opportunities. Any formulation must have suitable flow properties, not only to assist in the manufacture and metering of the powders, but also to provide reliable and predictable resuspension and fluidisation, and to avoid excessive retention of the powder within the dispensing device.

BRIEF DESCRIPTION OF THE DRAWINGS

FIG. 2, also noted as Table 1, shows the Hosokawa Powder Tester Results for Sorbolac 400 (Mechanofused).

FIG. 3, also noted as Table 2, shows the Hosokawa Powder Tester Results for Extra Fine Lactose.

FIG. 4, also noted as Table 3, shows the Hosokawa Powder Tester Results for Sorbolac 400 (Cyclomixed).

FIG. 5, also noted as Table 4, shows the Hosokawa Powder Tester Results for Micronised Lactose (Model Drug).

FIG. 6, also noted as Table 5, shows the Hosokawa Powder Tester Results for SU003 (Conventional "Large" Carrier).

DETAILED DESCRIPTION OF THE INVENTION

Figure 1:
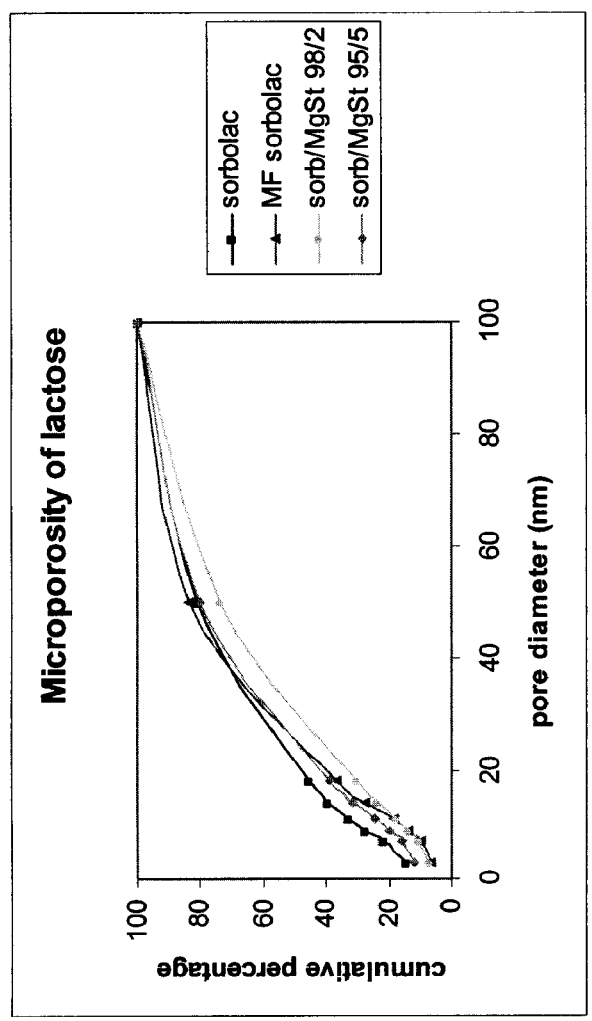
FIG. 1 shows the microporosity of various types of lactose particles as measured using the Cooker SA 3100 BET system as defined by pore diameter (nm) versus cumulative percentage.

The drug particles or particles of pharmaceutically active material (also referred to herein as "active" particles) in the resuspended powder must aerosolise into an ultra-fine aerosol so that they can be transported to the appropriate target area within the lung. Typically, for lung deposition, the active particles have a diameter of less than 10 μms, frequently 0.1 to 7 μm, 0.1 to 5 μm, or 0.5 to 5 μm.

For formulations to reach the deep lung or the blood stream via inhalation, the active agent in the formulation must be in the form of very fine particles, for example, having a mass median aerodynamic diameter (MMAD) of less than 10 μm. It is well established that particles having an MMAD of greater than 10 μm are likely to impact on the walls of the throat and generally do not reach the lung. Particles having an MMAD in the region of 5 to 2 μm will generally be deposited in the respiratory bronchioles whereas particles having an MMAD in the range of 3 to 0.05 μm are likely to be deposited in the alveoli and to be absorbed into the bloodstream.

Preferably, for delivery to the lower respiratory tract or deep lung, the MMAD of the active particles is not more than 10 μm, and preferably not more than more preferably not more than 3 μm, and may be less than 2 μm, less than 1.5 μm or less than 1 μm. Especially for deep lung or systemic delivery, the active particles may have a size of 0.1 to 3 μm or 0.1 to 2 μm.

Ideally, at least 90% by weight of the active particles in a dry powder formulation should have an aerodynamic diameter of not more than 10 μm, preferably not more than 5 μm, more preferably not more than 3 μm, not more than 2.5 μm, not more than 2.0 μm, not more than 1.5 μm, or even not more than 1.0 μm.

When dry powders are produced using conventional processes, the active particles will vary in size, and often this variation can be considerable. This can make it difficult to ensure that a high enough proportion of the active particles are of the appropriate size for administration to the correct site. It is therefore desirable to have a dry powder formulation wherein the size distribution of the active particles is as narrow as possible. For example, the geometric standard deviation of the active particle aerodynamic or volumetric size distribution ($\sigma g$), is preferably not more than 2, more preferably not more than 1.8, not more than 1.6, not more than 1.5, not more than 1.4, or even not more than 1.2. This will improve dose efficiency and reproducibility.

Fine particles, that is, those with an MMAD of less than 101. μm and smaller, tend to be increasingly thermodynamically unstable as their surface area to volume ratio increases, which provides an increasing surface free energy with this decreasing particle size, and consequently increases the tendency of particles to agglomerate and the strength of the agglomerate. In the inhaler, agglomeration of fine particles and adherence of such particles to the walls of the inhaler are problems that result in the fine particles leaving the inhaler as large, stable agglomerates, or being unable to leave the inhaler and remaining adhered to the interior of the inhaler, or even clogging or blocking the inhaler.

The uncertainty as to the extent of formation of stable agglomerates of the particles between each actuation of the inhaler, and also between different inhalers and different batches of particles, leads to poor dose reproducibility. Furthermore, the formation of agglomerates means that the MMAD of the active particles can be vastly increased, with agglomerates of the active particles not reaching the required part of the lung.

These micron to submicron particle sizes required for deep lung or systemic delivery lead to the problem that the respirable active particles tend to be highly cohesive, which means they generally exhibit poor flowability and poor aerosolisation.

To overcome the highly cohesive nature of such respirable active particles, formulators have, in the past, included larger carrier particles of an inert excipient in powder formulations, in order to aid both flowability and drug aerosolisation. Relatively large carrier particles have a beneficial effect on the powder formulations because, rather than sticking to one another, the fine active particles tend to adhere to the surfaces of the larger carrier particles whilst in the inhaler device. The active particles are supposed to release from the carrier particle surfaces and become dispersed upon actuation of the dispensing device, to give a fine suspension which may be inhaled into the respiratory tract. In general, it has been considered that the carrier particles should preferably have a mass median aerodynamic diameter (MMAD) of at least about 90 μm, and in general terms should preferably have a mass median aerodynamic diameter (MMAD) of greater than 40 μm, and not less than 20 μm.

However, whilst the addition of relatively large carrier particles does tend to improve the powder properties, it also has the effect of diluting the drug, usually to such an extent that 95% or more by total weight of the formulation is carrier. Relatively large amounts of carrier are required in order to have the desired effect on the powder properties because the majority of the fine or ultra-fine active particles need to adhere to the surfaces of the carrier particles, otherwise the cohesive nature of the active particles still dominates the powder and results in poor flowability. The surface area of the carrier particles available for the fine particles to adhere to decreases with increasing diameter of the carrier particles. However, the flow properties tend to become worse with decreasing diameter. Hence, there is a need to find a suitable balance in order to obtain a satisfactory carrier powder. An additional consideration is that one can get segregation if too few carrier particles are included, which is extremely undesirable.

An additional major problem experienced by formulators is the variability in surface properties of drug and excipient particles. Each active agent powder has its own unique inherent stickiness or surface energy, which can range tremendously from compound to compound. Further, the nature of the surface energies can change for a given compound depending upon how it is processed. For example, jet milling is notorious for generating significant variations in surface properties because of the aggressive nature of the collisions it employs. Such variations can lead to increased surface energy and increased cohesiveness and adhesiveness.

Even in highly regular, crystalline powders, the short range van der Waals forces (which include fixed dipole and similar fixed charge related forces and which depend on the chemistry of the functional groups exposed on the surface of the particles) can lead to highly cohesive and adhesive powders.

Solutions to some of the problems touched upon above are already known. For example, flow problems associated with larger amounts of fine material (for example, in powder formulations including relatively high proportions (such as up to from 5 to 20% by total weight of the formulation) of fine lactose or drug and fine lactose) may be overcome by use of a large fissured lactose as carrier particles, as discussed in earlier patent applications published as WO 01/78694, WO 01/78695 and WO 01/78696.

In order to improve the properties of powder formulations, and in particular to improve the flowability and dispersibility of the formulation, dry powder formulations often include additive materials which are intended to reduce the cohesion between the fine particles in the dry powder formulation. It is thought that the additive material interferes with the weak bonding forces between the small particles, helping to keep the particles separated and reducing the adhesion of such particles to one another, to other particles in the formulation if present and to the internal surfaces of the inhaler device. Where agglomerates of particles are formed, the addition of particles of additive material decreases the stability of those agglomerates so that they are more likely to break up in the turbulent air stream created on actuation of the inhaler device, where upon the particles are expelled from the device and inhaled.

In the prior art, dry powder formulations are discussed which include additive material (for example in the form of distinct particles of a size comparable to that of the fine active particles). In some embodiments, the additive material may be applied to and form a coating, generally a discontinuous coating, on the active particles or on any carrier particles.

Preferably, the additive material is an anti-adherent material and it will tend to reduce the cohesion between particles and will also prevent fine particles becoming attached to surfaces within the inhaler device. Advantageously, the additive material is an anti-friction agent or glidant and will give the powder formulation better flow properties in the inhaler. The additive materials used in this way may not necessarily be usually referred to as anti-adherents or anti-friction agents, but they will have the effect of decreasing the cohesion between the particles or improving the flow of the powder. As such, the additive materials are sometimes referred to as force control agents (FCAs) and they usually lead to better dose reproducibility and higher fine particle fractions (FPFs).

Therefore, an additive material or FCA, as used herein, is a material whose presence on the surface of a particle can modify the adhesive and cohesive surface forces experienced by that particle, in the presence of other particles and in relation to the surfaces that the particles are exposed to. In general, its function is to reduce both the adhesive and cohesive forces.

The reduced tendency of the particles to bond strongly, either to each other or to the device itself, not only reduces powder cohesion and adhesion, but can also promote better flow characteristics. This leads to improvements in the dose reproducibility because it reduces the variation in the amount of powder metered out for each dose and improves the release of the powder from the device. It also increases the likelihood that the active material which does leave the device will reach the lower lung of the patient.

It is favourable for unstable agglomerates of particles to be present in the powder when it is in the inhaler device. For a powder to leave an inhaler device efficiently and reproducibly, it is generally accepted that the particles should ideally be large, preferably larger than about 40 µm. Such a powder may be in the form of either individual particles having a size of about 40 µm or larger and/or agglomerates of finer particles, the agglomerates having a size of about 40 µm or larger. The agglomerates formed can have a size of as much as about 1000 µm and, with the addition of the additive material, those agglomerates are more likely to be broken down efficiently in the turbulent airstream created on inhalation. Therefore, the formation of unstable or "soft" agglomerates of particles in the powder may be favoured compared with a powder in which there is substantially no agglomeration. Such unstable agglomerates are retained whilst the powder is inside the device but are then disrupted and broken up when the powder is dispensed.

The use of additive materials in this manner is disclosed in two earlier patent applications, published as WO 96/23485 and WO 97/03649.

It is also known that intensive co-milling of micronised drug particles with additive material may be carried out in order to produce composite particles. This co-micronisation can improve dispersibility, as disclosed in the earlier patent application published as WO 02/43701. In addition, the earlier application published as WO 02/00197 discloses the intensive co-milling of fine particles of excipient material with additive material, to create composite excipient particles to which fine active particles and, optionally, coarse carrier particles may be added. This co-micronisation of fine excipient particles and additive material has also been shown to improve dispersibility.

Whilst the various disclosures in the prior art of the use of additive materials as force control agents do indicate improvements in powder properties (such as the dispersibility and flow) as a result of the addition of the additive material, the known powders and processing methods fail to provide the maximum effect possible with the optimum combination of small carrier and drug, and do not provide the maximum effect possible from the least necessary amount of additive material. The optimisation of the use of the additive material is important for several reasons. Firstly, it is clearly desirable to provide a dry powder formulation with the best possible powder properties in order to ensure efficient, reliable and accurate dosing. Secondly, it is also desirable to minimise the amount of the additive material (or indeed of any material) administered to the lung. This will reduce the risk of adverse effects that may be caused by the material. Thirdly, it is desirable to be able to deliver the maximum dose with optimum efficiency from a minimum powder payload, especially for high dose drugs. Finally, the use of as little additive material as possible will also be more economical. These features will also help to keep the device size small, maximise number of doses per device and reduce device complexity.

The present invention seeks to improve upon the powder formulations provided in the prior art, to ensure that their powder properties are optimised and the powder preparation is simple and economical.

It is also an object of the present invention to permit an increased percentage of ultra-fine drug to be used in a formulation, optionally with a fine carrier component, whilst still providing a powder formulation which exhibits improved flow, and improved aerosolisation due to the individually tailored surface conditioning of the respective drug and carrier particles.

It has been found that the most advantageous powder system incorporates one or more additives or force control agents on the surface of the both the drug particles and the carrier particles, in order to maximise the potential for flow and aerosolisation.

In the prior art, it is generally not suggested to attach the additive to both the active particles and carrier or excipient particles to obtain the advantages outlined here.

The minimum amount of the additive or FCA necessary to improve powder properties is preferably used, for toxicology and dosing reasons. What is more, the ideal incorporation of the additive is in the form of at least an approximate single minimum layer of additive material as a coating around each powder component, that is around both the active particles and any carrier particles present. As the drug particles are generally smaller (i.e. less than 5 µm), they will have a correspondingly higher surface area to volume ratio than the generally larger (>5 µm) carrier particles.

According to a first aspect of the present invention, a method of preparing a powder formulation is provided, the method comprising co-milling active particles with an additive material, separately co-milling carrier particles with an additive material, and then combining the co-milled active and carrier particles.

The co-milling steps preferably produce composite particles of active and additive material or carrier and additive material.

The powder formulations prepared according to the methods of the present invention exhibit excellent powder properties that may be tailored to the active agent, the dispensing device to be used and/or various other factors. In particular, the co-milling of active and carrier particles in separate steps allows different types of additive material and different quantities of additive material to be milled with the active and carrier particles. Consequently, the additive material can be selected to match its desired function, and the minimum amount of additive material can be used to match the relative surface area of the particles to which it is being applied.

In one embodiment, the active particles and the carrier particles are both co-milled with the same additive material or additive materials. In an alternative embodiment, the active and carrier particles are co-milled with different additive materials.

In one embodiment of the invention, active particles of less than about 5 µm diameter are co-milled with an appropriate amount of an additive or force control agent, whilst carrier particles with a median diameter in the range of about 3 µm to about 40 µm are separately co-milled with an appropriate amount of an additive.

Generally, the amount of additive co-milled with the carrier particles will be less, by weight, than that co-milled with the active particles. Nevertheless, the amount of additive used is kept to a minimum whilst being sufficient to have the desired effect on the powder properties. The treated drug and carrier particles are then combined to provide a formulation with the desired features.

The additive material is preferably in the form of a coating on the surfaces of the active and carrier particles. The coating may be a discontinuous coating. In another embodiment, the additive material may be in the form of particles adhering to the surfaces of the active and carrier particles. Preferably, the additive material actually becomes fused to the surfaces of the active and carrier particles It is advantageous for carrier particles to be used in the size range having a median diameter of about 3 to about 40 µm, preferably about 5 to about 30 µm, more preferably about 5 to about 20 µm, and most preferably about 5 to about 15 µm. Such particles, if untreated with an additive are unable to provide suitable flow properties when incorporated in a powder formulation comprising ultra-fine active particles. Indeed, previously, particles in these size ranges would not have been regarded as suitable for use as carrier particles, and instead would have been added in small quantities as a fine component. Such fine components are known to increase the aerosolisation properties of formulations containing a drug and a larger carrier, typically with median diameter 40 µm to 100 µm or greater. However, the amount of the fine components that may be included in such formulations is limited, and formulations including more than about 10% fines tend to exhibit poor properties unless special carrier particles are included, such as the large fissured lactose carrier particles mentioned above.

Alternatively, compositions of micronised drug and micronised lactose are known, but only where this blend has subsequently been successfully compressed and granulated into pellets. This process is generally very difficult to control and pellets are prone to destruction, resulting in powders with poor flow properties.

However, following treatment with additive materials, substantial changes in the powder characteristics of our fine carrier powders are seen. Powder density is increased, even doubled, for example from 0.3 g/cc to over 0.5 g/cc. Other powder characteristics are changed, for example, the angle of repose is reduced and contact angle increased.

Carrier particles having a median diameter of 3 to 40 µm are advantageous as their relatively small size means that they have a reduced tendency to segregate from the drug component, even when they have been treated with an additive, which will reduce cohesion. This is because the size differential between the carrier and drug is relatively small compared to that in conventional formulations which include ultra-fine active particles and much lager carrier particles. The surface area to volume ratio presented by the fine carrier particles is correspondingly greater than that of conventional large carrier particles. This higher surface area, allows the carrier to be successfully associated with higher levels of drug than for conventional larger carrier particles.

Carrier particles may be of any acceptable inert excipient material or combination of materials. For example, carrier particles frequently used in the prior art may be composed of one or more materials selected from sugar alcohols, polyols and crystalline sugars. Other suitable carriers include inorganic salts such as sodium chloride and calcium carbonate, organic salts such as sodium lactate and other organic compounds such as polysaccharides and oligosaccharides. Advantageously, the carrier particles comprise a polyol. In particular, the carrier particles may be particles of crystalline sugar, for example mannitol, dextrose or lactose. Preferably, the carrier particles are composed of lactose.

Advantageously, the additive material or FCA includes one or more compounds selected from amino acids and derivatives thereof, and peptides and derivatives thereof. Amino acids, peptides and derivatives of peptides are physiologically acceptable and give acceptable release of the active particles on inhalation.

It is particularly advantageous for the additive to comprise an amino acid. The additive may comprise one or more of any of the following amino acids: leucine, isoleucine, lysine, valine, methionine, and phenylalanine. The additive may be a salt or a derivative of an amino acid, for example aspartame or acesulfame K. Preferably, the additive consists substantially of an amino acid, more preferably of leucine, advantageously L-leucine. The D- and DL-forms may also be used. As indicated above, leucine has been found to give particularly efficient dispersal of the active particles on inhalation.

The additive may include one or more water soluble substances. This helps absorption of the additive by the body if it reaches the lower lung. The additive may include dipolar ions, which may be zwitterions. It is also advantageous to include a spreading agent as an additive, to assist with the dispersal of the composition in the lungs. Suitable spreading agents include surfactants such as known lung surfactants (e.g. ALEC™) which comprise phospholipids, for example, mixtures of DPPC (dipalmitoyl phosphatidylcholine) and PG (phosphatidylglycerol). Other suitable surfactants include, for example, dipalmitoyl phosphatidylethanolamine (DPPE), dipalmitoyl phosphatidylinositol (DPPI).

The additive may comprise a metal stearate, or a derivative thereof, for example sodium stearyl fumarate or sodium stearyl lactylate. Advantageously, it comprises a metal stearate, for example, zinc stearate, magnesium stearate, calcium stearate, sodium stearate or lithium stearate. Preferably, the additive material comprises magnesium stearate, for example vegetable magnesium stearate, or any form of commercially available metal stearate, which may be of vegetable or animal origin and may also contain other fatty acid components such as palmitates or oleates.

The additive may include or consist of one or more surface active materials, in particular materials that are surface active in the solid state, which may be water soluble or water dispersible, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof such as glyceryl behenate. Specific examples of such materials are phosphatidylcholines, phosphatidylethanolamines, phosphatidylglycerols and other examples of natural and synthetic lung surfactants; lauric acid and its salts, for example, sodium lauryl sulphate, magnesium lauryl sulphate; triglycerides such as Dynsan 118 and Cutina HR; and sugar esters in general. Alternatively, the additive may be cholesterol.

Other possible additive materials include sodium benzoate, hydrogenated oils which are solid at room temperature, talc, titanium dioxide, aluminium dioxide, silicon dioxide and starch. Also useful as additives are film-forming agents, fatty acids and their derivatives, as well as lipids and lipid-like materials.

In one embodiment of the invention, the additive comprises an amino acid, a derivative of an amino acid, a metal stearate or a phospholipid. Preferably, the additive comprises one or more of L-, D- or DL-forms of leucine, isoleucine, lysine, valine, methionine, phenylalanine, or Aerocine™, lecithin or magnesium stearate. In another embodiment, the additive comprises leucine and preferably L-leucine.

In some embodiments, a plurality of different additive materials can be used.

The present invention can be carried out with any pharmaceutically active agent. The terms "active particles" and "particles of active material" and the like are used interchangeably herein. The active particles comprise one or more pharmaceutically active agents. The preferred active agents include:

1) steroid drugs such as alcometasone, beclomethasone, beclomethasone dipropionate, betamethasone, budesonide, ciclesonide, clobetasol, deflazacort, diflucortolone, desoxymethasone, dexamethasone, fludrocortisone, flunisolide, fluocinolone, fluometholone, fluticasone, fluticasone propionate, hydrocortisone, triamcinolone, nandrolone decanoate, neomycin sulphate, rimexolone, methylprednisolone and prednisolone;

2) bronchodilators such as β2-agonists including salbutamol, formoterol, salmeterol, fenoterol, bambuterol, bitolterol, sibenadet, metaproterenol, epinephrine, isoproterenol, pirbuterol, procaterol, terbutaline and isoetharine antimuscarinics including ipratropium and tiotropium, and xanthines including aminophylline and theophylline;

3) nitrates such as isosorbide mononitrate, isosorbide dinitrate and glyceryl trinitrate;

4) antihistamines such as azelastine, chlorpheniramine, astemizole, cetirizine, cinnarizine, desloratadine, loratadine, hydroxyzine, diphenhydramine, fexofenadine, ketotifen, promethazine, trimeprazine and terfenadine;

5) anti-inflammatory agents such as piroxicam, nedocromil, benzydamine, diclofenac sodium, ketoprofen, ibuprofen, heparinoid, cromoglycate, fasafungine, iodoxamide and p38 MAP kinase inhibitors;

6) anticholinergic agents such as atropine, benzatropine, biperiden, cyclopentolate, oxybutinin, orphenadine, glycopyrronium, glycopyrrolate, procyclidine, propantheline, propiverine, tiotropium, trihexyphenidyl, tropicamide, trospium, ipratropium bromide and oxitroprium bromide;

7) leukotriene receptor antagonists such as montelukast and zafirlukast;

8) anti-allergics such as ketotifen;

9) anti-emetics such as bestahistine, dolasetron, nabilone, prochlorperazine, ondansetron, trifluoperazine, tropisetron, domperidone, hyoscine, cinnarizine, metoclopramide, cyclizine, dimenhydrinate and promethazine;

10) hormonal drugs (including hormone analogues) such as lanreotide, octreotide, insulin, pegvisomant, protirelin, thyroxine, salcotonin, somatropin, tetracosactide, vasopressin and desmopressin;

11) sympathomimetic drugs such as adrenaline, noradrenaline, dexamfetamine, dipirefin, dobutamine, dopexamine, phenylephrine, isoprenaline, dopamine, pseudoephedrine, tramazoline and xylometazoline;

12) opioids, preferably for pain management, such as buprenorphine, dextromoramide, dextropropoxypene, diamorphine, codeine, dextropropoxyphene, dihydrocodeine, hydromorphone, papaveretum, pholcodeine, loperamide, fentanyl, methadone, morphine, oxycodone, phenazocine, pethidine, tramadol and combinations thereof with an anti-emetic;

13) analgesics such as aspirin and other salicylates, paracetamol, clonidine, codine, coproxamol, ergotamine, gabapentin, pregabalin, sumatriptan, and non-steroidal anti-inflammatory drugs (NSAIDs) including celecoxib, etodolac, etoricoxib and meloxicam;

14) acetylcholinesterase inhibitors such as donepezil, galantamine and rivastigmine;

15) immunomodulators such as interferon (e.g. interferon beta-1a and interferon beta-1b) and glatiramer;

16) NMDA receptor antagonists such as mementine;

17) hypoglycaemics such as sulphonylureas including glibenclamide, gliclazide, glimepiride, glipizide and gliquidone, biguanides including metformin, thiazolidinediones including pioglitazone, rosiglitazone, nateglinide, repaglinide and acarbose;

18) narcotic agonists and opiate antidotes such as naloxone, and pentazocine;

19) phosphodiesterase inhibitors such as non-specific phosphodiesterase inhibitors including theophylline, theobromine, IBMX, pentoxifylline and papaverine; phosphodiesterase type 3 inhibitors including bipyridines such as milrinone, amrinone and olprinone; imidazolones such as piroximone and enoximone; imidazolines such as imazodan and 5-methyl-imazodan; imidazo-quinoxalines; and dihydropyridazinones such as indolidan and LY181512 (5-(6-oxo-1,4,5,6-tetrahydro-pyridazin-3-yl)-1,3-dihydro-indol-2-one); dihydroquinolinone compounds such as cilostamide, cilostazol, and vesnarinone; phosphodiesterase type 4 inhibitors such as cilomilast, etazolate, rolipram, roflumilast and zardaverine, and including quinazolinediones such as nitraquazone and nitraquazone analogs; xanthine derivatives such as denbufylline and arofylline; tetrahydropyrimidones such as atizoram; and oxime carbamates such as filaminast; and phosphodiesterase type 5 inhibitors including sildenafil, zaprinast, vardenafil, tadalafil, dipyridamole, and the compounds described in WO 01/19802, particularly (S)-2-(2-hydroxymethyl-1-pyrrolidinyl)-4-(3-chloro-4-methoxy-benzylamino)-5-[N¬(2-pyrimidinylmethyl)carbamoyl] pyrimidine, 2-(5,6,7,8-tetrahydro-1, 7-naphthyridin¬7-yl)-4-(3-chloro-4-methoxybenzylamino)-5-[N-(2-morpholinoethyl)carbamoyl]-pyrimidine, and (S)-2-(2-hydroxymethyl-1-pyrrolidinyl)-4-(3-chloro-4-methoxy¬benzylamino)-5[N-(1,3,5-trimethyl-4-pyrazolyl)carbamoyl]-pyrimidine);

20) antidepressants such as tricyclic and tetracyclic antidepressants including amineptine, amitriptyline, amoxapine, butriptyline, cianopramine, clomipramine, dosulepin, doxepin, trimipramine, clomipramine, lofepramine, nortriptyline, tricyclic and tetracyclic amitryptiline, amoxapine, butriptyline, clomipramine, demexiptiline, desipramine, dibenzepin, dimetacrine, dothiepin, doxepin, imipramine, iprindole, levoprotiline, lofepramine, maprotiline, melitracen, metapramine, mianserin, mirtazapine, nortryptiline, opipramol, propizepine, protriptyline, quinupramine, setiptiline, tianeptine and trimipramine; selective serotonin and noradrenaline reuptake inhibitors (SNRIs) including clovoxamine, duloxetine, milnacipran and venlafaxine; selective serotonin reuptake inhibitors (SSRIs) including citalopram, escitalopram, femoxetine, fluoxetine, fluvoxamine, ifoxetine, milnacipran, nomifensine, oxaprotiline, paroxetine, sertraline, sibutramine, venlafaxine, viqualine and zimeldine; selective noradrenaline reuptake inhibitors (NARIS) including demexiptiline, desipramine, oxaprotiline and reboxetine; noradrenaline and selective serotonin reuptake inhibitors (NASSAs) including mirtazapine; monoamine oxidase inhibitors (MAOIs) including amiflamine, brofaromine, clorgyline, α-ethyltryptamine, etoperidone, iproclozide, iproniazid, isocarboxazid, mebanazine, medifoxamine, moclobemide, nialamide, pargyline, phenelzine, pheniprazine, pirlindole, procarbazine, rasagiline, safrazine, selegiline, toloxatone and tranylcypromine; muscarinic antagonists including benactyzine and dibenzepin; azaspirones including buspirone, gepirone, ipsapirone, tandospirone and tiaspirone; and other antidepressants including amesergide, amineptine, benactyzine, bupropion, carbamazepine, fezolamine, flupentixol, levoprotiline, maprotiline, medifoxamine, methylphenidate, minaprine, nefazodone, nomifensine, oxaflozane, oxitriptan, rolipram, sibutramine, teniloxazine, tianeptine, tofenacin, trazadone, tryptophan, viloxazine, and lithium salts;

21) serotonin agonists such as 2-methyl serotonin, buspirone, ipsaperone, tiaspirone, gepirone, lysergic acid diethylamide, ergot alkaloids, 8-hydroxy-(2-N,N¬dipropylamino)-tetraline, 1-(4-bromo-2,5-dimethoxyphenyl)-2- aminopropane, cisapride, sumatriptan, m-chlorophenylpiperazine, trazodone, zacopride and mezacopride;

22) serotonin antagonists including ondansetron, granisetron, metoclopramide, tropisetron, dolasetron, trimethobenzamide, methysergide, risperidone, ketanserin, ritanserin, clozapine, amitryptiline, R(+)-α-(2,3-dimethoxyphenyl)-1[2-(4-fluorophenyl)ethyl]-4-piperidine-methanol, azatadine, cyproheptadine, fenclonine, dexfenfluramine, fenfluramine, chlorpromazine and mianserin;

23) adrenergic agonists including methoxamine, methpentermine, metaraminol, mitodrine, clonidine, apraclonidine, guanfacine, guanabenz, methyldopa, amphetamine, methamphetamine, epinephrine, norepinephrine, ethylnorepinephrine, phenylephrine, ephedrine, pseudo-ephedrine, methylphenidate, pemoline, naphazoline, tetrahydrozoline, oxymetazoline, xylometazoline, phenylpropanolamine, phenylethylamine, dopamine, dobutamine, colterol, isoproterenol, isotharine, metaproterenol, terbutaline, metaraminol, tyramine, hydroxyamphetamine, ritodrine, prenalterol, albuterol, isoetharine, pirbuterol, bitolterol, fenoterol, formoterol, procaterol, salmeterol, mephenterine and propylhexedrine;

24) adrenergic antagonists such as phenoxybenzamine, phentolamine, tolazoline, prazosin, terazosin, doxazosin, trimazosin, yohimbine, ergot alkaloids, labetalol, ketanserin, urapidil, alfuzosin, bunazosin, tamsulosin, chlorpromazine, haloperidol, phenothiazines, butyrophenones, propranolol, nadolol, timolol, pindolol, metoprolol, atenolol, esmolol, acebutolol, bopindolol, carteolol, oxprenolol, penbutolol, carvedilol, medroxalol, naftopidil, bucindolol, levobunolol, metipranolol, bisoprolol, nebivolol, betaxolol, carteolol, celiprolol, sotalol, propafenone and indoramin;

25) adrenergic neurone blockers such as bethanidine, debrisoquine, guabenxan, guanadrel, guanazodine, guanethidine, guanoclor and guanoxan;

26) benzodiazepines such as alprazolam, bromazepam, brotizolam, chlordiazepoxide, clobazam, clonazepam, clorazepate, demoxepam, diazepam, estazolam, flunitrazepam, flurazepam, halazepam, ketazolam, loprazolam, lorazepam, lormetazepam, medazepam, midazolam, nitrazepam, nordazepam, oxazepam, prazepam, quazepam, temazepam and triazolam;

27) mucolytic agents such as N-acetylcysteine, recombinant human DNase, amiloride, dextrans, heparin, desulphated heparin and low molecular weight heparin;

28) antibiotic and antibacterial agents such as metronidazole, sulphadiazine, triclosan, neomycin, amoxicillin, amphotericin, clindamycin, aclarubicin, dactinomycin, nystatin, mupirocin and chlorhexidine;

29) anti-fungal drugs such as caspofungin, voriconazole, polyene antibiotics including amphotericin, and nystatin, imidazoles and triazoles including clotrimazole, econazole nitrate, fluconazole, ketoconazole, itraconazole, terbinafine and miconazole;

30) antivirals such as oseltamivir, zanamivir, amantadine, inosine pranobex and palivizumab, DNA polymerase inhibitors including aciclovir, adefovir and valaciclovir, nucleoside analogues including famiciclovir, penciclovir and idoxuridine and interferons;

31) vaccines;

32) immunoglobulins;

33) local anaesthetics such as amethocaine, bupivacaine, hydrocortisone, methylprednisolone, prilocaine, proxymetacaine, ropivacaine, tyrothricin, benzocaine and lignocaine;

34) anticonvulsants such as sodium valproate, carbamazepine, oxcarbazepine, phenytoin, fosphenytoin, diazepam, lorazepam, clonazepam, clobazam, primidone, lamotrigine, levetiracetam, topiramate, gabapentin, pregabalin, vigabatrin, tiagabine, acetazolamide, ethosuximide and piracetam;

35) angiotensin converting enzyme inhibitors such as captopril, cilazapril, enalapril, fosinopril, imidapril hydrochloride, lisinopril, moexipril hydrochloride, perindopril, quinapril, ramipril and trandolapril;

36) angiotension II receptor blockers, such as candesartan, cilexetil, eprosartan, irbesartan, losartan, olmesartan medoxomil, telmisartan and valsartan;

37) calcium channel blockers such as amlodipine, bepridil, diltiazem, felodipine, flunarizine, isradipine, lacidipine, lercanidipine, nicardipine, nifedipine, nimodipine and verapamil;

38) alpha-blockers such as indoramin, doxazosin, prazosin, terazosin and moxisylate;

39) antiarrhythmics such as adenosine, propafenone, amidodarone, flecainide acetate, quinidine, lidocaine hydrochloride, mexiletine, procainamide and disopyramide;

40) anti-clotting agents such as aspirin, heparin and low molecular weight heparin, epoprostenol, dipyridamole, clopidogrel, alteplase, reteplase, streptokinase, tenecteplase, certoparin, heparin calcium, enoxaparin, dalteparin, danaparoid, fondaparin, lepirudin, bivalirudin, abciximab, eptifibatide, tirofiban, tinzaparin, warfarin, lepirudin, phenindione and acenocoumarol;

41) potassium channel modulators such as nicorandil, cromakalim, diazoxide, glibenclamide, levcromakalim, minoxidil and pinacidil;

42) cholesterol-lowering drugs such as colestipol, colestyramine, bezafibrate, fenofibrate, gemfibrozil, ciprofibrate, rosuvastatin, simvastatin, fluvastatin, atorvastatin, pravastatin, ezetimibe, ispaghula, nictotinic acid, acipimox and omega-3 triglycerides;

43) diuretics such as bumetanide, furosemide, torasemide, spironolactone, amiloride, bendroflumethiazide, chlortalidone, metolazone, indapamide and cyclopenthiazide;

44) smoking cessation drugs such as nicotine and bupropion;

45) bisphosphonates such as alendronate sodium, sodium clodronate, etidronate disodium, ibandronic acid, pamidronate disodium, isedronate sodium, tiludronic acid and zoledronic acid;

46) dopamine agonists such as amantadine, bromocriptine, pergolide, cabergoline, lisuride, ropinerole, pramipexole and apomorphine;

47) nucleic-acid medicines such as oligonucleotides, decoy nucleotides, antisense nucleotides and other gene-based medicine molecules;

48) antipsychotics such as: dopamine antagonists including chlorpromazine, prochlorperazine, fluphenazine, trifluoperazine and thioridazine; phenothiazines including aliphatic compounds, piperidines and piperazines; thioxanthenes, butyrophenones and substituted benzamides; atypical antipsychotics including clozapine, risperidone, olanzapine, quetiapine, ziprasidone, zotepine, amisulpride and aripiprazole; and 49) pharmaceutically acceptable salts or derivatives of any of the foregoing.

In preferred embodiments of the present invention, the active agent is heparin (fractionated and unfractionated), apomorphine, clobazam, clomipramine or glycopyrrolate.

In addition, the active agents used in the present invention may be small molecules, proteins, carbohydrates or mixtures thereof.

The term co-milling is used herein to refer to a range of methods, including co-micronising methods, some examples of which are outlined below. In the prior art, co-milling or co-micronising active agents or excipients with additive materials has been suggested.

It is stated that milling can be used to substantially decrease the size of particles of active agent. However, if the particles of active agent are already fine, for example have a MMAD of less than 20 μm prior to the milling step, the size of those particles may not be significantly reduced where the milling of these active particles takes place in the presence of an additive material. Rather, milling of fine active particles with additive particles using the methods described in the prior art (for example, in the earlier patent application published as WO 02/43701) will result in the additive material becoming deformed and being smeared over or fused to the surfaces of the active particles. The resultant composite active particles have been found to be less cohesive following the milling treatment.

The prior art mentions two types of processes in the context of co-milling or co-micronising active and additive particles. First, there is the compressive type process, such as Mechanofusion and the Cyclomix and related methods such as the Hybridiser or the Nobilta. As the name suggests, Mechanofusion is a dry coating process designed to mechanically fuse a first material onto a second material. The first material is generally smaller and/or softer than the second. The principles behind the Mechanofusion and Cyclomix processes are distinct from those of alternative milling techniques in that they have a particular interaction between an inner element and a vessel wall, and in that they are based on providing energy by a controlled and substantial compressive force.

The fine active particles and the additive particles are fed into the Mechanofusion driven vessel (such as a Mechanofusion system (Hosokawa Micron Ltd)), where they are subject to a centrifugal force which presses them against the vessel inner wall. The inner wall and a curved inner element together form a gap or nip in which the particles are pressed together. The powder is compressed between the fixed clearance of the drum wall and a curved inner element with high relative speed between drum and element. As a result, the particles experience very high shear forces and very strong compressive stresses as they are trapped between the inner drum wall and the inner element (which has a greater curvature than the inner drum wall). The particles are pressed against each other with enough energy to locally heat and soften, break, distort, flatten and wrap the additive particles around the active particles to form coatings. The energy is generally sufficient to break up agglomerates and some degree of size reduction of both components may occur. Whilst the coating may not be complete, the deagglomeration of the particles during the process ensures that the coating may be substantially complete, covering the majority of the surfaces of the particles.

These Mechanofusion and Cyclomix processes apply a high enough degree of force to separate the individual particles of active material and to break up tightly bound agglomerates of the active particles such that effective mixing and effective application of the additive material to the surfaces of those particles is achieved.

An especially desirable aspect of the described co-milling processes is that the additive material becomes deformed during the milling and may be smeared over or fused to the surfaces of the active particles. However, in practice, this compression process produces little or no size reduction of the drug particles, especially where they are already in a micronised form (i.e. <10 μm). The only physical change which may be observed is a plastic deformation of the particles to a rounder shape.

However the most preferred milling techniques include those described in R. Pfeffer et al. "*Synthesis of engineered particulates with tailored properties using dg particle coating*", Powder Technology 117 (2001) 40-67. These include processes using the MechanoFusion® machine, the Hybidizer® machine, the Theta Composer®, magnetically assisted impaction processes and rotating fluidised bed coaters. Cyclomix methods may also be used.

Preferably, the technique employed to apply the required mechanical energy involves the compression of a mixture of particles of the dispersing agent and particles of the pharmaceutically active agent in a nip formed between two portions of a milling machine, as is the case in the MechanoFusion® and Cyclomix devices. Some preferred milling methods will now be described in greater detail:

MechanoFusion®:

As the name suggests, this dry coating process is designed to mechanically fuse a first material onto a second material. The first material is generally smaller and/or softer than the second. The MechanoFusion and Cyclomix working principles are distinct from alternative milling techniques in having a particular interaction between inner element and vessel wall, and are based on providing energy by a controlled and substantial compressive force.

The fine active particles and the particles of dispersing agent are fed into the MechanoFusion driven vessel, where they are subject to a centrifugal force and are pressed against the vessel inner wall. The powder is compressed between the fixed clearance of the drum wall and a curved inner element with high relative speed between drum and element. The inner wall and the curved element together form a gap or nip in which the particles are pressed together. As a result the particles experience very high shear forces and very strong compressive stresses as they are trapped between the inner drum wall and the inner element (which has a greater curvature than the inner drum wall). The particles violently collide against each other with enough energy to locally heat and soften, break, distort, flatten and wrap the particles of dispersing agent around the core particle to form a coating. The energy is generally sufficient to break up agglomerates and some degree of size reduction of both components may occur. Embedding and fusion of additive particles of dispersing agent onto the active particles may occur, and may be facilitated by the relative differences in hardness (and optionally size) of the two components. Either the outer vessel or the inner element may rotate to provide the relative movement. The gap between these surfaces is relatively small, and is typically less than 10 mm and is preferably less than 5 mm, more preferably less than 3 mm. This gap is fixed, and consequently leads to a better control of the compressive energy than is provided in some other forms of mill such as ball and media mills. Also, in general, no impaction of milling media surfaces is present so that wear and consequently contamination are minimised. The speed of rotation may be in the range of 200 to 10,000 rpm. A scraper may also be present to break up any caked material building up on the vessel surface. This is particularly advantageous when using fine cohesive starting materials. The local temperature may be controlled by use of a heating/cooling hacked built into the drum vessel walls. The powder may be re-circulated through the vessel.

Cyclomix Method (Hosokawa Microm):

The cyclomix comprises a stationary conical vessel with a fast rotating shaft with paddles which move close to the wall. Due to the high rotational speed of the paddles, the powder is propelled towards the wall, and as a result the mixture experiences very high shear forces and compressive stresses between wall and paddle. Such effects are similar to those in MechanoFusion as described above and may be sufficient to locally heat and soften, to break, distort, flatten and wrap the particles of dispersing agent around the active particles to form a coating. The energy is sufficient to break up agglomerates and some degree of size reduction of both components may also occur depending on the conditions and upon the size and nature of the particles.

Hybridiser® Method:

This is a dry process which can be described as a product embedding or filming of one powder onto another. The fine active particles and fine or ultra fine particles of dispersing agent are fed into a conventional high shear mixer pre-mix system to form an ordered mixture. This powder is then fed into the Hybridiser. The powder is subjected to ultra-high speed impact, compression and shear as it is impacted by blades on a high speed rotor inside a stator vessel, and is re-circulated within the vessel. The active and additive particles collide with each other. Typical speeds of rotation are in the range of 5,000 to 20,000 rpm. The relatively soft fine particles of dispersing agent experience sufficient impact force to soften, break, distort, flatten and wrap around the active particle to form a coating. There may also be some degree of embedding into the surface of the active particles.

The second of the types of processes mentioned in the prior art is the impact milling processes. Such impact milling is involved, for example, in ball milling, jet milling and the use of a homogeniser.

Ball milling is a milling method used in many of the prior art co-milling processes. Centrifugal and planetary ball milling are especially preferred methods.

Jet mills are capable of reducing solids to particle sizes in the low-micron to submicron range. The grinding energy is created by gas streams from horizontal grinding air nozzles. Particles in the fluidised bed created by the gas streams are accelerated towards the centre of the mill, colliding with slower moving particles. The gas streams and the particles carried in them create a violent turbulence and, as the particles collide with one another, they are pulverized.

High pressure homogenisers involve a fluid containing the particles being forced through a valve at high pressure, producing conditions of high shear and turbulence. Suitable homogenisers include EmulsiFlex high pressure homogenisers which are capable of pressures up to 4000 bar, Niro Soavi high pressure homogenisers (capable of pressures up to 2000 bar) and Micro fluidics Microfluidisers (maximum pressure 2750 bar).

Milling may, alternatively, involve a high energy media mill or an agitator bead mill, for example, the Netzsch high energy media mill, or the DYNO-mill (Willy A. Bachofen AG, Switzerland).

All of these processes create high-energy impacts between media and particles or between particles. In practice, while these processes are good at making very small particles, it has been found that the ball mill, jet mill and the homogenizer were not as effective in producing dispersion improvements in resultant drug powders as the compressive type processes. It is believed that the impact processes discussed above are not as effective in producing a coating of additive material on each particle as the compressive type processes.

For the purposes of this invention, all forms of co-milling and co-micronisation are encompassed, including methods that are similar or related to all of those methods described above. For example, methods similar to Mechanofusion are encompassed, such as those utilizing one or more very high-speed rotors (i.e. 2000 to 50000 rpm) with blades or other elements sweeping the internal surfaces of the vessels with small gaps between wall and blade (i.e. 0.1 mm to 20 mm). Conventional methods comprising co-milling active material with additive materials (as described in WO 02/43701) are also encompassed. These methods result in composite active particles comprising ultra-fine active particles with an amount of the additive material on their surfaces.

Thus, the milling methods used in the present invention are simple and cheap compared to the complex previous attempts to engineer particles, providing practical as well as cost benefits. A further benefit associated with the present invention is that the powder processing steps do not have to involve organic solvents. Such organic solvents are common to many of the known approaches to powder processing and are known to be undesirable for a variety of reasons.

In the past, jet milling has been considered less attractive for co-milling active and additive particles in the preparation of powder formulations to be dispensed using passive devices, with compressive processes like or related to Mechanofusion and Cyclomixing being preferred. The collisions between the particles in a jet mill are somewhat uncontrolled and those skilled in the art, therefore, considered it unlikely that this technique would be able to provide the desired deposition of a coating of additive material on the surface of the active particles.

Moreover, it was believed that, unlike the situation with compressive type processes such as Mechanofusion and Cyclomixing, segregation of the powder constituents occurred in jet mills, such that the finer particles, that were believed to be the most effective, could escape from the process. In contrast, it could be clearly envisaged how techniques such as Mechanofusion would result in the desired coating.

However, more recently, jet milling has been shown to be an attractive process for co-milling active and additive particles, especially for preparing powder formulations that are to be used in active devices (see the disclosure in the earlier patent application published as WO 2004/001628).

It should also be noted that it was also previously believed that the compressive or impact milling processes must be carried out in a closed system, in order to prevent segregation of the different particles. This has also been found to be untrue and the co-milling processes used in the present invention do not need to be carried out in a closed system. In an open system, the co-jet milling has surprisingly been found not to result in the loss of the small particles, even when using leucine as the additive material. Leucine was previously considered to present something of a problem when co-jet milled.

Further, co-jet milling at lower pressures can produce powders which perform well in passive devices whilst powders milled at higher pressures may perform better in active devices, such as Aspirair™.

The co-milling processes can be specifically selected for the active and carrier particles. For example, the active particles may be co-jet milled or homogenized with the additive, whilst the carrier particles may be mechanofused with the additive.

The co-milling processes according to the present invention may be carried out in two or more stages, to provide beneficial effects. Various combinations of types of co-milling and/or additive material may be used, in order to obtain advantages. Within each step, multiple combinations of co-milling and other processing steps may be used.

For example, milling at different pressures and/or different types of milling or blending processes may be combined. The use of multiple steps allows one to tailor the properties of the milled particles to suit a particular inhaler device, a particular drug and/or to target particular parts of the lung.

In one embodiment of the present invention, the milling process is a two-step process comprising first jet milling the drug on its own at suitable grinding pressure to obtain the required particle sizes. Next, the milled drug is co-milled with an additive material. Preferably, this second step is carried out at a lower grinding pressure, so that the effect achieved is the coating of the small active particles with the additive material. This two-step process may produce better results than simply co-milling the active material and additive material at a high grinding pressure.

The same type of two-step milling process can be carried out with the carrier particles, although these particles, as a rule, do not have to be milled to such small particle sizes.

In another embodiment of the present invention, the composite particles, which may optionally have been produced using the two-step co-milling process discussed above, subsequently undergo Mechanofusion. This final Mechanofusion step may "polish" the composite particles, further rubbing the additive material into the particles. This provides beneficial properties afforded by Mechanofusion, in combination with the very small particles sizes made possible by the co jet milling. Such an additional Mechanofusion step is particularly attractive for composite active particles, especially where they are very small.

The reduction in particle size may be increased by carrying out the co-jet milling at lower temperatures. Whilst the co jet milling process may be carried out at temperatures between −20° C. and 40° C., the particles will tend to be more brittle at lower temperatures and they therefore fracture more readily so that the milled particles tend to be even smaller. Therefore, in another embodiment of the present invention, the jet milling is carried out at temperatures below room temperature, preferably at a temperature below 10° C., more preferably at a temperature below 0° C.

The benefits of the methods according to the present invention are illustrated by the experimental data set out below.

COMPARATIVE EXAMPLES

Example 1

Mechanofused Budesonide with Magnesium Stearate

This example studied magnesium stearate processed with budesonide. The blends were prepared by Mechanofusion using the Hosokawa AMS-MINI, with blending being carried out for 60 minutes at approximately 4000 rpm.

The magnesium stearate used was a standard grade supplied by Avocado Research Chemicals Ltd. The drug used was micronised budesonide. The powder properties were tested using the Miat Monohaler.

Blends of budesonide and magnesium stearate were prepared at different weight percentages of magnesium stearate. Blends of 5% w/w and 10% w/w, were prepared and then tested. MSLIs and TSIs were carried out on the blends. The results, which are summarised below, indicate a high aerosolisation efficiency. However, this powder had poor flow properties, and was not easily handled, giving high device retention.

| Formulation | FPF (ED) | FPD (mg) | ED (mg) | Method |
|---|---|---|---|---|
| Budesonide:magnesium stearate (5% w/w) | 73% | 1.32 | 1.84 | MSLI |
| Budesonide:magnesium stearate (10% w/w) | 80% | 1.30 | 1.63 | TSI |

Example 2

Mechanofused Budesonide with Fine Lactose and Magnesium Stearate

A further study was conducted to look at the Mechanofusion of a drug with both a force control agent and fine lactose particles. The additive or force control agent used was magnesium stearate (Avocado) and the fine lactose was Sorbolac 400 (Meggle). The drug used was micronised budesonide.

The blends were prepared by Mechanofusion of all three components together using the Hosokawa AMS-MINI, blending was carried out for 60 minutes at approximately 4000 rpm.

Formulations were prepared using the following concentrations of budesonide, magnesium stearate and Sorbolac 400:

5% w/w budesonide, 6% w/w magnesium stearate, 89% w/w Sorbolac 400; and

20% w/w budesonide, 6% w/w magnesium stearate, 74% w/w Sorbolac 400.

TSIs and MSLIs were performed on the blends. The results, which are summarised below, indicate that, as the amount of budesonide in the blends increased, the FPF results increased. Device and capsule retention were notably low in these dispersion tests (<5%), however a relatively large level of magnesium stearate was used and this was applied over the entire composition.

| Formulation | FPF(ED) (TSI) | FPF(ED) (MSLI) |
|---|---|---|
| 5:6:89 | 66.0% | 70.1% |
| 20:6:74 | 75.8% | — |

As an extension to this work, different blending methods of budesonide, magnesium stearate and Sorbolac 400 were investigated further. Two formulations were prepared in the Glen Creston Grindomix. This mixer is a conventional food-processor style bladed mixer, with 2 parallel blades.

The first of these formulations was a 5% w/w budesonide, 6% w/w magnesium stearate, 89% w/w Sorbolac 400 blend prepared by mixing all components together at 2000 rpm for 20 minutes. The formulation was tested by TSI and the results, when compared to those for the mechanofused blends, showed the Grindomix blend to give lower FPF results (see table below).

The second formulation was a blend of 90% w/w of mechanofused magnesium stearate:Sorbolac 400 (5:95) pre-blend and 10% w/w budesonide blended in the Grindomix for 20 minutes. The formulation was tested by TSI and MSLI.

It was also observed that this formulation had notably good flow properties for a material comprising such fine particles. This is believed to be associated with the Mechanofusion process.

| Formulation | FPF (ED) (TSI) | FPF (MSLI) |
| --- | --- | --- |
| Grindomix 5:6:89% | 57.7 | — |
| Grindomix 10% budesonide (Mechanofused pre-blend) | 65.9 | 69.1 |

Example 3

Mechanofused Salbutamol with Fine Lactose and Magnesium Stearate

A further study was conducted to look at the Mechanofusion of an alternative drug with both a force control agent and fine lactose particles. The additive or force control agent used was magnesium stearate and the fine lactose was Sorbolac 400 (Meggle). The drug used was micronised salbutamol sulphate. The blends were prepared by Mechanofusion using the Hosokawa AMS-MINI, blending for 10 minutes at approximately 4000 rpm.

Formulations prepared were:
20% w/w salbutamol, 5% w/w magnesium stearate, 75% w/w Sorbolac 400; and
20% w/w salbutamol, 2% w/w magnesium stearate, 78% w/w Sorbolac 400.

NGIs were performed on the blends and the results are set out below. Device and capsule retention were again low in these dispersion tests (<10%).

| Formulation | FPF (ED) | FPF (ED) |
| --- | --- | --- |
| 20:5:75 | 80% | 74% |
| 20:2:78 | 78% | 70% |

Example 4

Preparation of Mechanofused Formulation for Use in a Passive Device 20 g of a mix comprising 20% micronised clomipramine, 78% Sorbolac 400 (fine lactose) and 2% magnesium stearate were weighed into the Hosokawa AMS-MINI Mechanofusion system via a funnel attached to the largest port in the lid with the equipment running at 3.5%. The port was sealed and the cooling water switched on. The equipment was run at 20% for 5 minutes followed by 80% for 10 minutes. The equipment was switched off, dismantled and the resulting formulation recovered mechanically.

20 mg of the collected powder formulation was filled into size 3 capsules and fired from a Miat Monohaler into an NGI. The FPF measured was good, being greater than 70%.

The data above suggest that magnesium stearate content in the region 5-20% yielded the greatest dispersibility. Above these levels, experience suggests significant sticking inside the device could occur, and the quantities used became unnecessary for further performance improvement.

Fine particle fraction values were consistently obtained in the range 50 to 60%, and doubled in comparison with controls containing no magnesium stearate.

EXAMPLES OF THE INVENTION

Example 5

Mechanofused Apomorphine and Mechanofused Fine Lactose

Firstly, 15 g of micronised apomorphine and 0.75 g leucine are weighed into the Hosokawa AMS-MINI Mechanofusion system via a funnel attached to the largest port in the lid with the equipment running at 3.5%. The port is sealed and the cooling water switched on. The equipment is run at 20% for 5 minutes followed by 80% for 10 minutes. The equipment is then switched off, dismantled and the resulting formulation recovered mechanically.

Next, 19 g of Sorbolac 400 lactose and 1 g leucine are weighed into the Hosokawa AMS-MINI Mechanofusion system via a funnel attached to the largest port in the lid with the equipment running at 3.5%. The port is sealed and the cooling water switched on. The equipment is run at 20% for 5 minutes followed by 80% for 10 minutes. The equipment is switched off, dismantled and the resulting formulation recovered mechanically.

4.2 g of the apomorphine-based material and 15.8 g of the Sorbolac-based material are combined in a high shear mixer for 5 minutes, and the resulting powder is then passed through a 300 micron sieve to form the final formulation. 2 mg of the powder formulation are filled into blisters and fired from an Aspirair device into an NGI. An FPF of over 50% was obtained with MMAD 1.5 microns, illustrating this system gave a very good dispersion. The device retention was also very low, with only—1% left in the device and 7% in the blister.

Example 6

Mechanofused Clomipramine and Mechanofused Fine Lactose

Firstly, 20 g of a mix comprising 95% micronised clomipramine and 5% magnesium stearate are weighed into the Hosokawa AMS-MINI Mechanofusion system via a funnel attached to the largest port in the lid with the equipment running at 3.5%. The port is sealed and the cooling water switched on. The equipment is run at 20% for 5 minutes followed by 80% for 10 minutes. The equipment is then switched off, dismantled and the resulting formulation recovered mechanically.

Next, 20 g of a mix comprising 99% Sorbolac 400 lactose and 1% magnesium stearate are weighed into the Hosokawa AMS-MINI Mechanofusion system via a funnel attached to the largest port in the lid with the equipment running at 3.5%. The port is sealed and the cooling water switched on. The equipment is run at 20% for 5 minutes followed by 80% for 10 minutes. The equipment is switched off, dismantled and the resulting formulation recovered mechanically.

4 g of the clomipramine-based material and 16 g of the Sorbolac-based material are combined in a high shear mixer for 10 minutes, to form the final formulation. 20 mg of the powder formulation are filled into size 3 capsules and fired from a Miat Monohaler into an NGI.

Example 7

Mechanofused Theophylline and Mechanofused Fine Lactose

Firstly, 20 g of a mix comprising 95% micronised theophylline and 5% magnesium stearate are weighed into the Hosokawa AMS-MINI Mechanofusion system via a funnel attached to the largest port in the lid with the equipment running at 3.5%. The port is sealed and the cooling water switched on. The equipment is run at 20% for 5 minutes followed by 80% for 10 minutes. The equipment is then switched off, dismantled and the resulting formulation recovered mechanically.

Next, 20 g of a mix comprising 99% Sorbolac 400 lactose and 1% magnesium stearate are weighed into the Hosokawa AMS-MINI Mechanofusion system via a funnel attached to the largest port in the lid with the equipment running at 3.5%. The port is sealed and the cooling water switched on. The equipment is run at 20% for 5 minutes followed by 80% for 10 minutes. The equipment is switched off, dismantled and the resulting formulation recovered mechanically.

4 g of the theophylline-based material and 16 g of the Sorbolac-based material are combined in a high shear mixer for 10 minutes, to form the final formulation. 20 mg of the powder formulation are filled into size 3 capsules and fired from a Miat Monohaler into an NGI.

The active agent used in this example, theophylline, may be replaced by other phosphodiesterase inhibitors, including phosphodiesterase type 3, 4 or 5 inhibitors, as well as other non-specific ones.

Example 8

Jet Milled Clomipramine and Mechanofused Fine Lactose 20 g of a mix comprising 95% micronised clomipramine and 5% magnesium stearate are co-jet milled in a Hosokawa AS50 jet mill.

20 g of a mix comprising 99% Sorbolac 400 (fine lactose) and 1% magnesium stearate are weighed into the Hosokawa AMS-MINI Mechanofusion system via a funnel attached to the largest port in the lid with the equipment running at 3.5%. The port is sealed and the cooling water switched on. The equipment is run at 20% for 5 minutes followed by 80% for 10 minutes. The equipment is switched off, dismantled and the resulting formulation recovered mechanically.

4 g of the clomipramine-based material and 16 g of the Sorbolac-based material are combined in a high shear mixer for 10 minutes, to form the final formulation. 20 mg of the powder formulation are filled into size 3 capsules and fired from a Miat Monohaler into an NGI.

A number of micronised drugs were co-jet milled with magnesium stearate for the purposes of replacing the clomipramine in this example. These micronised drugs included budesonide, formoterol, salbutamol, glycopyrrolate, heparin, insulin and clobazam. Further compounds are considered suitable, including the classes of active agents and the specific examples listed above.

Example 9

Jet Milled Bronchodilator and Mechanofused Fine Lactose 20 g of a mix comprising 95% micronised bronchodilator drug and 5% magnesium stearate are co jet milled in a Hosokawa AS50 jet mill.

20 g of a mix comprising 99% Sorbolac 400 lactose and 1% magnesium stearate are weighed into the Hosokawa AMS-MINI Mechanofusion system via a funnel attached to the largest port in the lid with the equipment running at 3.5%. The port is sealed and the cooling water switched on. The equipment is run at 20% for 5 minutes followed by 80% for 10 minutes. The equipment is switched off, dismantled and the resulting formulation recovered mechanically.

4 g of the drug based material and 16 g of the Sorbolac based material are combined in a high shear mixer for 10 minutes, to form the final formulation.

20 mg of the powder formulation is filled into size 3 capsules and fired from a Miat Monohaler into an NGI.

The results of these experiments are expected to show that the powder formulations prepared using the method according to the present invention exhibit further improved properties such as FPD, FPF, as well as good flow and reduced device retention and throat deposition.

In accordance with the present invention, the % w/w of additive material will typically vary. Firstly, when the additive material is added to the drug, the amount used is preferably in the range of 0.1% to 50%, more preferably 1% to 20%, more preferably 2% to 10%, and most preferably 3 to 8%. Secondly, when the additive material is added to the carrier particles, the amount used is preferably in the range of 0.01% to 30%, more preferably of 0.1% to 10%, preferably 0.2% to 5%, and most preferably 0.5% to 2%. The amount of additive material preferably used in connection with the carrier particles will be heavily dependant upon the size and hence surface area of these particles.

Example 10

Lactose Study

A study was conducted to characterize the changes in the properties of fine carrier particles, and of ultra-fine drug particles, when they are co-milled with an additive material.

Micronised ultra-fine lactose was selected as a model for a drug, as it is readily available in a micronised form and it carries a reduced hazard compared to handling pharmaceutically active substances. Ultra-fine lactose is also regarded as a particularly cohesive material, hence improving its dispersibility represents a severe challenge.

Meggle Sorbolac 400 and Meggle Extra Fine were selected as the fine carrier grades, as these are readily available. However other lactose grades can be used, such as those produced by DMV, Borculo, Foremost and other suppliers, or a grade custom-made for the purpose, as long as it conforms to the size range indicated.

The literature reveals various possible types of tests, including measuring powder flow, powder cohesion, powder shear and powder dustiness.

In the first instance, several basic powder characteristics were tested. These were porosity and surface area using the Coulter SA 3100 BET system, and particle size, which was measured using a Mastersizer 2000, manufactured by Malvern Instruments, Ltd. (Malvern, UK). This was followed by examining several standard powder properties using the Hosokawa Powder Tester.

Porosity

The powder porosity was measured using the Coulter SA 3100 BET system, with the following results.

| Sample | Total pore volume (ml/g) |
| --- | --- |
| Sorbolac | 0.0027 |
| Mechanofused Sorbolac (60 mins) | 0.0044 |
| Mechanofused Sorbolac and magnesium stearate (98:2) (60 mins) | 0.0056 |

-continued

| Sample | Total pore volume (ml/g) |
|---|---|
| Mechanofused Sorbolac and magnesium stearate (95:5) (60 mins) | 0.0052 |

The microporosity of the lactose particles is also shown in the graph of FIG. 1. Whilst the total pore volume does increase significantly upon processing, insufficient differences are seen in the different pore sizes to use porosity testing as a measure of the process. Therefore, Malvern particle sizing of a wet powder dispersion was also conducted. The results are summarised below.

| Sample | Surface Area ($m^2/g$) | Malvern $d_{50}$ (gm) |
|---|---|---|
| Sorbolac | 1.023 | 8.760 |
| Magnesium Stearate | 13.404 | 9.145 |
| Mechanofused Sorbolac (60 mins) | 1.189 | 7.525 |
| Mechanofused Sorbolac and magnesium stearate (98:2) (0 mins) | 1.562 | 8.191 |
| Mechanofused Sorbolac and magnesium stearate (98:2) (60 mins) | 1.496 | 9.112 |
| Mechanofused Sorbolac and magnesium stearate (95:5) (0 mins) | 2.028 | 8.281 |
| Mechanofused Sorbolac and magnesium stearate (95:5) (60 mins) | 0.961 | 8.551 |
| Extra fine lactose | 0.798 | 16.523 |
| Mechanofused Extra fine lactose (60 mins) | 0.714 | 18.139 |
| Mechanofused Extra fine lactose and magnesium stearate (98:2) (60 mins) | 1.195 | 17.703 |
| Cyclomixed Sorbolac (60 mins) | 1.629 | 7.894 |
| Cyclomixed Sorbolac and magnesium stearate (98:2) (0 mins) | 1.617 | |
| Cyclomixed Sorbolac and magnesium stearate (98:2) (5 mins) | 1.473 | |
| Cyclomixed Sorbolac and magnesium stearate (98:2) (10 mins) | 1.442 | |
| Cyclomixed Sorbolac and magnesium stearate (98:2) (20 mins) | 1.383 | |
| Cyclomixed Sorbolac and magnesium stearate (98:2) (40 mins) | 1.404 | |
| Cyclomixed Sorbolac and magnesium stearate (98:2) (60 mins) | 1.425 | |
| Cyclomixed Sorbolac and magnesium stearate (95:5) (0 mins) | 1.779 | |

Whilst the surface area does decrease as the processing time increased, this can probably be explained as being due to the magnesium stearate becoming smeared over the surface.

Hosokawa Powder Tester

This system measures several different parameters, including: angle of repose; aerated bulk density; packed bulk density; angle of spatula before and after impact; angle of fall; and dispersibility.

The system then calculates further parameters/indices, including: angle of difference (repose–fall); compressibility (Cans index); average angle of spatula; and uniformity (based on $d_{10}$ and $d_{60}$).

Various powders were tested using this system and the resulting data are summarised in Tables 1 to 5, shown in FIGS. 2 to 6 respectively.

As can be seen from the data, on processing with magnesium stearate (Mg St), virtually all of the powders showed a tendency to decrease the angle of repose and the angle of fall, and to increase in bulk density and dispersibility.

For the Sorbolac 400 and the ultra-fine lactose, which are within the size range considered suitable for use as the carrier according to the present invention, the powders mechnofused with magnesium stearate show very considerable drops in the angle of repose and the angle of fall, as well as increases in aerated bulk, compared to the raw material (see Tables 1 and 2). Where the powder is mixed using a low shear mix, in this study a Turbula mixer was used, none of these changes are observed (see Table 1).

Table 3 shows Sorbolac 400 Cyclomixed with magnesium stearate. In these examples, considerable drops in the angle of repose and the angle of fall are observed, as well as increases in aerated bulk density. However, these changes are generally slightly less than those observed when the Sorbolac 400 and magnesium stearate are mechanofused. This is consistent with the increasing intensity of the processing methods producing increasing levels of effect.

Table 4 shows micronised lactose, which in these tests is used to represent a model micronised drug. Unfortunately, the variability of the results was higher and the data provided, especially for the angle of repose, the angle of fall for the raw material, was regarded as unreliable. The density increased but was still relatively low. These powders were observed as being highly cohesive. Even after Mechanofusion only slight improvements were seen, in contrast to the dramatic visible powder changes for Sorbolac 400 and the ultra-fine lactose.

Table 5 shows SV003, a traditional large lactose carrier material. In this case, the powder mechanofused with magnesium stearate shows smaller drops in the angle of repose and no change in the angle of fall (where it remains at an already low level in its original state). Similarly, the aerated bulk density increased slightly, but from an already high level.

Thus, the results indicate that the co-milled carrier particles within the preferred size range for the present invention and co-milled model drug particles showed a tendency to decrease in angle of repose, to increase in bulk density and to increase in dispersibility. These properties would be anticipated in conjunction with reduced cohesion. This improvement was observed to increase with increasing intensity of the co-milling methods and with increasing levels of additive material (magnesium stearate). The result is an improvement in performance of a formulation containing this carrier in an inhaler, in terms of improved emitted dose and in terms of improved fine particle dose, especially the fine particle dose of metered dose.

The metered dose (MD) of a dry powder formulation is the total mass of active agent present in the metered form presented by the inhaler device in question. For example, the MD might be the mass of active agent present in a capsule for a Cyclohaler™, or in a foil blister in a Gyrohaler™ device.

The emitted dose (ED) is the total mass of the active agent emitted from the device following actuation. It does not include the material left on the internal or external surfaces of the device, or in the metering system including, for example, the capsule or blister. The ED is measured by collecting the total emitted mass from the device in an apparatus frequently identified as a dose uniformity sampling apparatus (DUSA), and recovering this by a validated quantitative wet chemical assay (a gravimetric method is possible, but this is less precise).

The fine particle dose (FPD) is the total mass of active agent which is emitted from the device following actuation which is present in an aerodynamic particle size smaller than a defined limit. This limit is generally taken to be 5 μm if not expressly stated to be an alternative limit, such as 3 μm, 2 μm or 1 μm, etc. The FPD is measured using an impactor or impinger, such as a twin stage impinger (TSI), multi-stage impinger (MSI), Andersen Cascade Impactor (ACI) or a Next Generation Impactor (NGI). Each impactor or impinger has a pre-determined aerodynamic particle size collection cut points for each stage. The FPD value is obtained by interpretation of the stage-by-stage active agent recovery quantified by a validated quantitative wet chemical assay (a gravimetric method is possible, but this is less precise) where either a simple stage cut is used to determine FPD or a more complex mathematical interpolation of the stage-by-stage deposition is used.

The fine particle fraction (FPF) is normally defined as the FPD divided by the ED and expressed as a percentage. Herein, the FPF of ED is referred to as FPF(ED) and is calculated as FPF(ED)=(FPD/ED)×100%.

The fine particle fraction (FPF) may also be defined as the FPD divided by the MD and expressed as a percentage. Herein, the FPF of MD is referred to as FPF(MD), and is calculated as FPF(MD)=(FPD/MD)×100%.

Flodex Measurement

A means of assessing powder flow is to use the Flodex™ powder tester (Hansen Research).

The Flodex provides an index, over a scale of 4 to 40 mm, of flowability of powders. The analysis may be conducted by placing 50 g of a formulation into the holding chamber of the Flodex via a funnel, allowing the formulation to stand for 1 minutes, and then releasing the trap door of the Flodex to open an orifice at the base of the holding chamber. Orifice diameters of 4 to 34 mm can be used to measure the index of flowability. The flowability of a given formulation is determined as the smallest orifice diameter through which flow of the formulation is smooth.

Carr's Index

A formulation may be characterised by its density/flowability parameters and uniformity of distribution of the active ingredient. The apparent volume and apparent density can be tested according to the method described in the European Pharmacopoeia (Eur. Ph.).

Powder mixtures (100 g) are poured into a glass graduated cylinder and the unsettled apparent volume $V_0$ is read; the apparent density before settling (dv) was calculated dividing the weight of the sample by the volume $V_0$. After 1250 taps with the described apparatus, the apparent volume after settling ($V_{1250}$) is read and the apparent density after settling (ds) was calculated. The flowability properties were tested according to the method described in the Eur. Ph.

Powder mixtures (about 110 g) are then poured into a dry funnel equipped with an orifice of suitable diameter that is blocked by suitable means. The bottom opening of the funnel is unblocked and the time needed for the entire sample to flow out of the funnel recorded. The flowability is expressed in seconds and tenths of seconds related to 100 g of sample.

The flowability can also be evaluated from the Carr's index calculated according to the following formula: Carr's index (%)=((ds−dv)/ds)×100

A Carr index of less than 25 is usually considered indicative of good flowability characteristics.

The uniformity of distribution of the active ingredient may be evaluated by withdrawing 10 samples, each equivalent to about a single dose, from different parts of the blend. The amount of active ingredient of each sample can be determined by High-Performance Liquid Chromatography (HPLC).

Determination of the Aerosol Performances

An amount of powder for inhalation may be tested by loading it into a dry powder inhaler and firing the dose into an impactor or impinger, using the methods as defined in the European or US Pharmacopoeias.

SEM

This is a potentially useful method which may be used to identify powders exhibiting low cohesion, large magnesium stearate agglomerates, and changes in surface morphology following processing and/or segregation.

Differential Scanning Calorimetry (DSC) & Inverse Gas Chromatography (IGC)

These techniques may be useful for quantifying the surface energy and production of amorphous material during the processing of the powder particles. Amorphous material is regarded as potentially harmful to the long-term stability of powder formulations, making them prone to recrystallisation.

Powder characterisation parameters such as flowability indices or forms of surface characterisation have been considered. The Hosokawa Powder Tester provided a good test to qualify changes in powder properties. The mechano-fused powders showed a tendency to decrease in angle of repose, increase in bulk density and increase in dispersibility. However, as the particles approach the micron size, these Hosokawa Powder Tester tests were less equivocal. Also, these parameters may not be directly linked to performance during aerosolisation.

As well as characterizing the drug and fine carrier component powders, these Hosokawa Powder Tester tests are also helpful in characterizing the final combined formulation, where the final formulation properties are advantageously similar to the properties of the co-milled fine carrier. Consequently, the combined formulation will have good flow properties and provide low device retention.

Further, the good dispersibility of the drug component is retained, providing high levels of fine particle fraction and fine particle dose, as measured by standard in vitro tests. Such improvements are also consistent, providing less variability in the test results obtained than for traditional formulation approaches.

Another very important advantage of the system of the present invention is the consistency of the high performance. One of the many benefits of consistency is that it can also lead to reduction in adverse side effects experienced, as it will allow one to administer a smaller total dose than is possible when relying upon conventional levels of inhaler efficiency or other routes of administration. In particular, it allows one to target specific dosing windows wherein the therapeutic effect is maximised whilst causing the minimum side effects.

According to a second aspect of the present invention, formulations which are obtainable by the methods according to the first aspect of the invention are provided.

In powder compositions of the present invention, at least some of the composite particles may be in the form of agglomerates, preferably unstable agglomerates. However, when the composite active particles are included in a pharmaceutical composition, the additive material promotes the dispersal of the composite active particles on administration of that composition to a patient, via actuation of an inhaler. In the turbulence created upon actuation of the inhaler device, the agglomerates break up, releasing the composite particles of respirable size.

The powder particles according to the present invention, which may be prepared as described herein, are not "low density" particles, as tend to be favoured in the prior art. Such low density particles can be difficult and expensive to prepare. Indeed, previously, those skilled in the art have only reported high performance in connection with powder particles that have been prepared using fancy processing techniques such as complex spray drying, which result in low density particles. In contrast, the particles of the present invention are made using very simple and economical processes.

In contrast to the suggestion in the prior art, it may be advantageous not to produce severely dimpled or wrinkled particles as these can yield low density powders, with very high voidage between particles. Such powders have been reported as having good flow and dispersion characteristics, but they occupy a large volume relative to their mass as a consequence of their shape and can result in packaging problems, i.e. require much larger blisters or capsules to hold a given mass of powder.

In one embodiment of the present invention, the powders have a tapped density of at least 0.1 g/cc, at least 0.2 g/cc, at least 0.3 g/cc, at least 0.4 g/cc or at least 0.5 g/cc.

Example 11

Surface Chemical Analysis of Powders

The aim of the analysis is to identify the presence of magnesium stearate on the surface of a model co-micronised powder. The model powders were processed in two different ways, with one representing a conventional pharmaceutical blending process, and the other being the intensive Mechanofusion process which is the subject of the invention. The aim was to show the contrast in surface coating efficiency. In this case the model material was micronised lactose, which could represent a micronised drug or a fine carrier.

The powders have been analyzed using both TOF-SIMS and XPS. TOF-SIMS provides a mass spectrum of the outermost 1 nm of the surface, and is used here to assess whether the magnesium stearate coverage of the lactose is complete or in patches. XPS provides a spectrum representative of the outermost 10 nm of the surface of the sample and is used here in comparison to the TOF-SIMS data to assess the depth of coverage of the magnesium stearate on the lactose surface.

In addition, the powders were studied using the Zetasizer 3000HS instrument (Malvern Instruments Ltd, UK.) Each sample was tested in cyclohexane, and zeta potential measurements were obtained.

The following powder samples were prepared for testing:
Lactose;
Lactose/Magnesium Stearate 19/1 mixed by Turbula mixer; and
Lactose/Magnesium Stearate 19/1 mixed by Mechanofusion.

TOF-SIMS

SIMS is a qualitative surface analytical technique that is capable of producing a high-resolution mass spectrum of the outermost 1 nm of a surface.

In brief, the SIMS process involves bombarding the sample surface with a beam of primary ions (for example caesium or gallium). Collision of these ions with atoms and molecules in the surface results in the transfer of energy to them, causing their emission from the surface. The types of particles emitted from the surface include positive and negative ions (termed secondary ions), neutral species and electrons. Only secondary ions are measured in SIMS. Depending on the type of bias applied to the sample, either positive or negative ions are directed towards a mass spectrometer. These ions are then analysed in terms of their mass-to-charge ratio (m/¬) yielding a positive or negative ion mass spectrum of counts detected versus m/¬. Different fragments will be diagnostic of different components of the surface. TOF-SIMS is an advanced technique that has increased sensitivity (<<parts per million (ppm) sensitivity), mass resolution and mass range compared to conventional SIMS techniques. SIMS operating in static mode was used to determine the chemical composition of the top monolayer of the surface. Under static SIMS conditions, the primary ion dose is limited so that statistically the sample area analysed by the rastered ion beam is exposed to the beam once only, and that the spectrum generated is representative of a pristine surface.

TOF-SIMS analysis of the Turbula mixed sample (Lactose/Magnesium Stearate 19/1 mixed by Turbula) indicated the presence of both lactose and magnesium stearate in both positive and negative mass spectra, as shown in the table below. The presence of lactose in the spectra indicates that the surface coverage of magnesium stearate is incomplete.

TOF-SIMS analysis of the Mechanofusion mixed sample (Lactose/Magnesium Stearate 19/1 co-milled by Mechanofusion) also indicated the presence of both lactose and magnesium stearate in both positive and negative mass spectra. The presence of lactose in the spectra indicates that the surface coverage of magnesium stearate is incomplete.

It is important to note that SIMS spectra are not quantitative and so the intensities of the peaks cannot be taken to reflect the degree of surface coverage.

XPS

XPS is a surface analytical technique that can quantify the amount of different chemical species in the outermost 10 nm of a surface. In the simplest form of analysis, XPS measures the relative amount of each element present. Quantitative elemental identification can be achieved down to 1 atom in 1000. All elements present can be detected with the exception of hydrogen. Elemental analysis may be essential in determining the amount of a surface contaminant or to quantify any surface species with a unique elemental type.

| Sample | Relative Atomic Percentage Composition (%) | | |
| --- | --- | --- | --- |
| | C | O | Mg |
| Lactose | | | |
| Measurement 1 | 54.47 | 45.43 | Nd* |
| Measurement 2 | 55.29 | 44.71 | Nd* |
| Mean | 54.9 | 45.1 | <0.1 |
| Lactose/Magnesium Stearate (Turbula) | | | |
| Measurement 1 | 61.23 | 38.00 | 0.44 |
| Measurement 2 | 60.40 | 39.02 | 0.50 |
| Mean | 60.8 | 38.5 | 0.5 |
| Lactose/Magnesium Stearate (Mechanofusion) | | | |
| Measurement 1 | 81.39 | 17.07 | 1.51 |
| Measurement 2 | 80.72 | 17.80 | 1.49 |
| Mean | 81.1 | 17.4 | 1.5 |

*Nd = not detected (<0.1 atomic %)

XPS analysis of the Lactose/Magnesium Stearate 19/1 sample mixed by Turbula revealed the presence of magnesium on the surface of the lactose indicating the presence of magnesium stearate. Using the percentage presence of magnesium on the surface it is calculated that the magnesium stearate contributes 20% of the overall signal from the outermost 10 nm of the sample surface. Peak fitting the carbon 1s envelope enables the identification and quantification of the functionalities present at the surface. The clear increase in C—H/C—C carbon centres at the surface is ascribed to the coverage of magnesium stearate and demonstrates a similar degree of signal intensity to that predicted from the magnesium abundance.

XPS analysis of the Lactose/Magnesium Stearate 19/1 Mechanofusion mixed sample again demonstrates the presence of magnesium stearate on the lactose surface by both the magnesium abundance and the increase in C—C/C—H functionality over that seen on pure lactose. Using the percentage of magnesium in the spectrum the magnesium stearate is calculated to contribute 61.5% of the signal from the outermost 10 nm of the sample surface. An increase of similar magnitude is observed for the C—C/C—H coverage.

The carboxyl functionality present on the surface of the lactose can most likely be attributed to surface contamination, and as such the carboxyl group is not used to assess the degree of magnesium stearate coverage. However for the two mixed samples the extent of carboxyl functionality follows the same trend as for magnesium and the C—C/C—H increases.

The Mechanofusion mixed sample demonstrated significantly increased amounts of magnesium stearate at the surface, over the Turbula mixed sample. These differences could reflect either a thickening of the coverage of magnesium stearate or an increased surface coverage given the incomplete coverage as demonstrated by TOF-SIMS analysis.

| Sample | Area % of C 1 s Spectral Envelope | | | |
|---|---|---|---|---|
| | C—C | C—O | O—C—O | O—C=O |
| Lactose | | | | |
| Measurement 1 | 6.4 | 70.9 | 18.0 | 4.7 |
| Measurement 2 | 4.4 | 57.8 | 22.0 | 12.8 |
| Mean | 5.5 | 64.3 | 20.0 | 8.7 |
| Lactose/Magnesium Stearate (Turbula) | | | | |
| Measurement 1 | 25.8 | 57.5 | 14.7 | 2.1 |
| Measurement 2 | 24.7 | 58.8 | 15.0 | 1.6 |
| Mean | 25.2 | 58.1 | 14.8 | 1.8 |
| Lactose/Magnesium Stearate (Mechanofusion) | | | | |
| Measurement 1 | 75.7 | 16.1 | 3.9 | 4.3 |
| Measurement 2 | 73.9 | 17.2 | 4.5 | 4.5 |
| Mean | 74.8 | 16.6 | 4.2 | 4.4 |

In conclusion both mixed samples demonstrate an incomplete coverage of magnesium stearate, but with about three times more magnesium stearate present on the Mechanofusion mixed sample than the Turbula sample in the top 10 nm of the surface.

Zeta Potential

Zetasizer measures the zeta potential. This is a measure of the electric potential on a particle in suspension in the hydrodynamic plane of shear. The results are summarized as follows:

| Sample | Zeta Potential (mV) |
|---|---|
| Lactose | 35.5 |
| Lactose/Magnesium Stearate (19/1) (Turbula) | 4.8 |
| Lactose/Magnesium Stearate (19/1) (Mechanofusion) | −34.8 |

Figure 7:
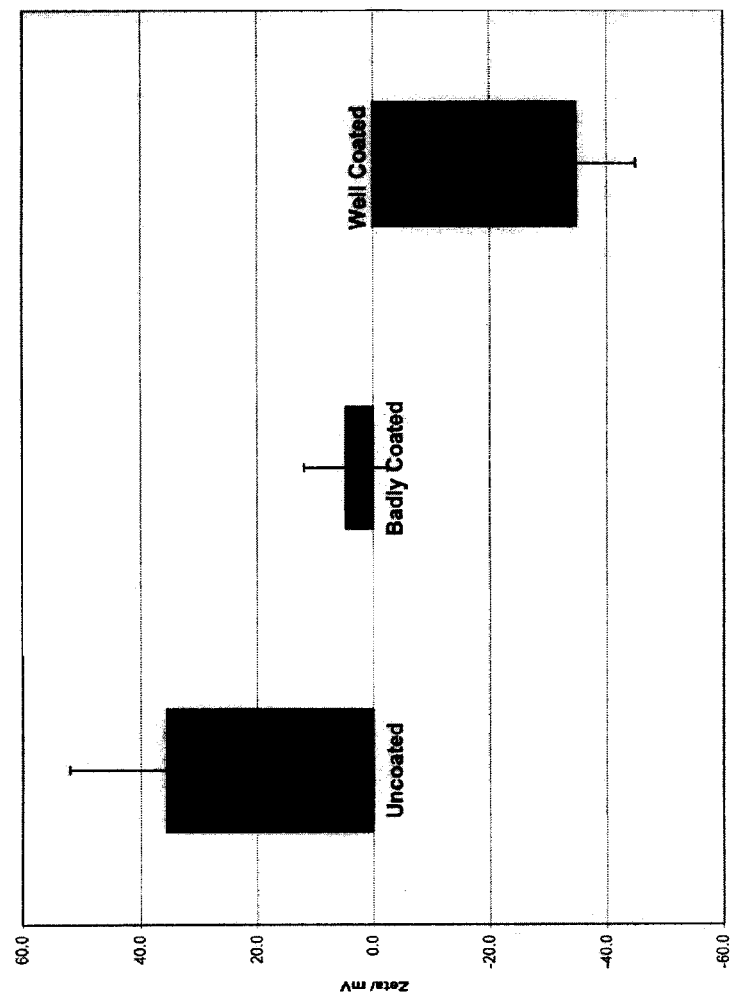
FIG. 7 shows the zeta potential of Lactose. Lactose/Magnesium Stearate that has been Turbula-blended and Lactose/Magnesium Stearate that has been mechanofused.

Each result is an average of 10 measurements. The data are presented in FIG. 7. This technique shows a clear difference in the zeta potential measurements, as a function of surface coating process, where the improved covering of magnesium stearate is indicated by an increasingly negative zeta potential.

These results demonstrate that applying the additive material to fine or ultra-fine carrier or active particles by conventional mixing or blending, for example using a low shear mixer like a Turbula mixer, does not provide the same improvement in powder performance as the use of the co-milling process according to the present invention. The latter processes appear to literally fuse the additive material to the surfaces of the active or carrier particles.

The powders of the present invention are extremely flexible and therefore have a wide number of applications, for both local application of drugs in the lungs and for systemic delivery of drugs via the lungs.

The present invention is also applicable to nasal delivery, and powder formulations intended for this alternative mode of administration to the nasal mucosa.

The formulations according to the present invention may be administered using active or passive devices, as it has now been identified how one may tailor the formulation to the device used to dispense it, which means that the perceived disadvantages of passive devices where high performance is sought may be overcome.

According to a third aspect of the present invention, a dry powder device is provided, the device comprising a powder formulation according to the second aspect of the invention.

In one embodiment of the invention, the inhaler device is an active device, in which a source of compressed gas or alternative energy source is used. Examples of suitable active devices include Aspirair™ (Vectura Ltd) and the active inhaler device produced by Nektar Therapeutics (as covered by U.S. Pat. No. 6,257,233).

In an alternative embodiment, the inhaler device is a passive device, in which the patient's breath is the only source of gas which provides a motive force in the device. Examples of "passive" dry powder inhaler devices include the Rotahaler™ and Diskhaler™ (GlaxoSmithKline) and the Turbohaler™ (Astra-Draco) and Novolizer™ (Viatris GmbH).

The size of the doses can vary from micrograms to tens of milligrams. The fact that dense particles may be used, in contrast to conventional thinking, means that larger doses can be administered without needing to administer large volumes of powder and the problems associated therewith.

The dry powder formulations may be pre-metered and kept in foil blisters which offer chemical and physical protection whilst not being detrimental to the overall performance. Indeed, the formulations thus packaged tend to be stable over long periods of time, which is very beneficial, especially from a commercial and economic point of view.

According to a fourth aspect of the present invention, a receptacle is provided, holding a single dose of a powder according to the second aspect of the present invention.

The receptacle may be a capsule or blister, preferably a foil blister.

What is claimed:

1. A powder formulation comprising an active, magnesium stearate and lactose, wherein the active is a $\beta_2$ agonist, wherein the powder formulation incorporates magnesium stearate on the surface of both the active particles and the lactose particles, wherein when the magnesium stearate is added to the lactose, the amount used is from 0.5 to 2 wt % of the weight of the lactose, and wherein when the magnesium stearate is added to the active, the amount used is from 0.1 to 50 wt % of the weight of the active.

2. The powder formulation according to claim 1, the formulation being obtainable by co-milling of active particles with magnesium stearate, separately co-milling lactose particles with magnesium stearate, and combining the co-milled active and co-milled lactose particles.

3. The powder formulation according to claim 1 wherein magnesium stearate forms a discontinuous coating on the surfaces of the active and lactose particles.

4. The powder formulation according to claim 2 wherein magnesium stearate forms a discontinuous coating on the surfaces of the active and lactose particles.

5. The powder formulation according to claim 4 wherein the powder formulation has a tapped density of at least 0.1 g/cc.

6. The powder formulation according to claim 1 wherein the powder formulation has a tapped density of at least 0.1 g/cc.

7. The powder formulation according to claim 1 which is a passive device powder formulation.

8. The powder formulation according to claim 1, wherein the $\beta_2$ agonist is salmeterol.

9. The powder formulation according to claim 1, wherein when the magnesium stearate is added to the active, the amount used is from 1 to 20 wt % of the weight of the active.

10. A dry powder inhaler device comprising a powder formulation according to claim 1 wherein the device is a passive device.

11. A dry powder inhaler device comprising a powder formulation according to claim 2 wherein the device is a passive device.

12. A dry powder inhaler device comprising a powder formulation according to claim 3 wherein the device is a passive device.

13. A dry powder inhaler device comprising a powder formulation according to claim 4 wherein the device is a passive device.

14. A dry powder inhaler device comprising a powder formulation according to claim 5 wherein the device is a passive device.

15. A dry powder inhaler device comprising a powder formulation according to claim 6 wherein the device is a passive device.

16. A dry powder inhaler device comprising a powder formulation according to claim 7 wherein the device is a passive device.

\* \* \* \* \*